US008551920B2

(12) United States Patent
Hoet et al.

(10) Patent No.: US 8,551,920 B2
(45) Date of Patent: Oct. 8, 2013

(54) LIBRARIES AND METHODS FOR ISOLATING ANTIBODIES

(75) Inventors: Rene Hoet, Maastricht (NL); Sonia Schoonbroodt, Lixhe (BE); Robert C. Ladner, Ijamsville, MD (US)

(73) Assignee: Morpho Sys AG, Martinsried/Planegg (DE)

( * ) Notice: Subject to any disclaimer, the term of this patent is extended or adjusted under 35 U.S.C. 154(b) by 1204 days.

(21) Appl. No.: 11/346,403

(22) Filed: Feb. 1, 2006

(65) Prior Publication Data

US 2006/0234302 A1    Oct. 19, 2006

Related U.S. Application Data

(60) Provisional application No. 60/649,065, filed on Feb. 1, 2005.

(51) Int. Cl.
*C40B 30/04*    (2006.01)
*C40B 20/08*    (2006.01)
*C40B 50/06*    (2006.01)

(52) U.S. Cl.
USPC .................................... 506/9; 506/6; 506/26

(58) Field of Classification Search
USPC .................................................. 506/6, 9, 26
See application file for complete search history.

(56) References Cited

U.S. PATENT DOCUMENTS

| | | | |
|---|---|---|---|
| 5,869,644 A * | 2/1999 | Shortle et al. | 536/25.3 |
| 5,872,215 A * | 2/1999 | Osbourne et al. | 530/387.3 |
| 5,962,255 A * | 10/1999 | Griffiths et al. | 435/69.1 |
| 6,764,835 B2 | 7/2004 | Short | |
| 6,846,634 B1 * | 1/2005 | Tomlinson et al. | 506/9 |
| 2006/0257937 A1 | 11/2006 | Ladner | |

FOREIGN PATENT DOCUMENTS

| WO | WO97/20932 | | 6/1997 |
|---|---|---|---|
| WO | WO98/39027 | | 9/1998 |
| WO | WO 02/061071 | * | 8/2002 |
| WO | 2004065416 | | 8/2004 |

OTHER PUBLICATIONS

Dennissen et al., 2002, JBC, 277(13): 10982-10986.*
Jenniskens et al., 2000, J. Neuroscience, 20(1): 4099-4111.*
Westerlo et al., 2002, Blood, 99(7): 2427-2433.*
Nguyen et al., 2003, Nature Structural Biology, 10(12): 1019-1025.*
Cardin et al., 1989, Arteriosclerosis, 9: 21-32.*
Nissim et al., 1994, Antibody fragments from a single pot phage display library as immunochemical reagents, The EMBO Journal, 13(3): 692-698.*
Akamatsu et al., 1993, Construction of a Human Ig Combinatorial Library from Genomic V segments and Synthetic CDR3 Fragments, The Journal of Immunology, 151(9): 4651-4659.*
Bernsen et al., "Heparan Sulphate Epitope-Expression is Associated with the Inflammatory Response in Metastatic Malignant Melanoma", Cancer Immunol Immunother, vol. 52, pp. 780-783, (2003).
Brummell et al., "Probing the Combining Site of an Anti-Carbohydrate Antibody by Saturation-Mutagenesis: Role of the Heavy-Chain CDR3 Residues", Biochemistry, vol. 32, pp. 1180-1187, (1993).
Cardin and Weintraub, "Molecular Modeling of Protein-Glycosaminoglycan Interactions", Arteriosclerosis, vol. 9, pp. 21-32, (1989).
Chang & Siegel, "Isolation of an IgG Anti-B from a Human Fab-Phage Display Library", Transfusion, vol. 41, pp. 6-12, (2001).
Chen et al., "Genes Coding Evolutionary Novel Anti-Carbohydrate Antibodies: Studies on Anti-Gal Production in α1,3galactosyltransferase Knock Out Mice", Molecular Immunology, vol. 37, pp. 455-466, (2000).
Chen et al., "Induction of Heparin-Binding EGF-like Growth Factor Expression during Myogenesis", The Journal of Biological Chemistry, vol. 270, No. 31, pp. 18285-18294, (1995).
Danielsson et al., "Human monoclonal antibodies with different fine specificity for digoxin derivatives: cloning of heavy and light chain variable region sequences", Immunology, vol. 74, pp. 50-54, (1991).
Dennissen et al., "Large, Tissue-regulated Domain Diversity of Heparan Sulfates Demonstrated by Phage Display Antibodies", The Journal of Biological Chemistry, vol. 277, pp. 10982-10986, (2002).
Dinh et al., "High Affinity Antibodies Against Le$^x$ and Sialyl Le$^x$ from a Phage Display Library", The Journal of Immunology, vol. 157, pp. 732-738, (1996).
Dube et al., "Glycans in Cancer and Inflammation—Potential for Therapeutics and Diagnostics", Nature Drug Discovery Reviews, vol. 4, pp. 477-488, (2005).
Fischback and Rosen, "ARIA: A Neurimuscular Junction Neuregulin", Annu. Rev. Neurosci., vol. 20, pp. 429-458, (1997).
Foy et al., "Characterization of a Unique Human Single-Chain Antibody Isolated by Phage-Display Selection on Membrane-Bound Mosquito Midgut Antigens", Journal of Immunological Methods, vol. 261, pp. 73-83, (2002).
Haidaris et al., "Recombinant Human Antibody Single Chain Variable Fragments Reactive with *Candida albicans* Surface Antigens", Journal of Immunological Methods, vol. 257, pp. 185-202, (2001).
Hoet et al., "Generation of High-Affinity Human Antibodies by Combining Donor-Derived and Synthetic Complementarity-Determining-Region Diversity", Nature Biotechnology, vol. 23, No. 3, pp. 344-348, (2005).
Jeffrey et al., "The X-ray structure of an Anti-Tumor Antibody in complex with Antigen", Nature Structural Biology, vol. 2, No. 5, pp. 466-471, (1995).
Jenniskens et al., "Heparan Sulfate Heterogeneity in Skeletal Muscle Basal Lamina: Demonstration by Phage Display-Derived Antibodies", The Journal of Neuroscience, vol. 20, pp. 4099-4111, (2000).
Kawashima et al., "N-acetylglucosamine-6-O-sulfotransferases 1 and 2 Cooperatively Control Lymphocyte Homing Through L-selectin Ligand Biosynthesis in High Endothelial Venules", Nature Immunology, vol. 6, No. 11, pp. 1096-1104, (2005).

(Continued)

*Primary Examiner* — Amber D Steele
(74) *Attorney, Agent, or Firm* — Paul F. Wiegel

(57) ABSTRACT

The disclosure features methods for identifying antibodies that bind to a carbohydrate moiety. Libraries coding for antibodies that bind to a carbohydrate moiety are provided. The libraries can be provided by modifying a pre-existing nucleic acid library. Antibodies that bind to a carbohydrate moiety are described.

14 Claims, 14 Drawing Sheets

(56) References Cited

OTHER PUBLICATIONS

Komar et al., Dependence of Conformational Stability of an Immunoglogulin variable Domain on CDR Sequence, Biological-Chemistry Hoppe-Seyler, vol. 372, (1991) (abstract).
Kowal et al., "Molecular Mimicry Between Bacterial and Self Antigen in a Patient with Systemic Lupus Erythematosus", European Journal of Immunology, vol. 29, pp. 1901-1911, (1999).
Lee et al., "Phage-Display Selection of a Human Single-Chain Fv Antibody Highly Specific for Melanoma and Breast Cancer Cells Using a Chemoenzymatically Synthesized $G_{M3}$- Carbohydrate Antigen", J. Am. Chem. Soc., vol. 124, pp. 12439-12446, (2002).
Mackenzie and To, "The role of valency in the selection of anti-carbohydrate single chain Fvs from phage display libraries", Journal of Immunological Methods, vol. 22, pp. 39-49 (1998).
Marks et al., "By-Passing Immunization: Human Antibodies from V-Gene Libraries Displayed on Phage", J. Mo;. Biol. vol. 222, pp. 581-597, (1991).
Mao et al., "Phage-Display Library Selection of High-Affinity Human Single-Chain Antibodies to Tumor-Associated Carbohydrate Antigens Sialyl Lewis$^x$ and Lewis$^y$" Proc. Natl. Acad. Sci. USA, vol. 96, pp. 6953-6958, (1999).
Nguyen et al., "Germline Anitbody Recognition of Distinct Carbohydrate Epitopes", Nature Structural Biology, vol. 10 No. 12, pp. 1019-1025, (2003).
Pratt and Bertozzi, "Synthesis of 6-Sulfo Sialyl Lewis X Glycans Corresponding to the L-Selectin Ligan "Sulfoadhesin"", Organic Letters, vol. 6, No. 14, pp. 2345-2348, (2004).
Reason et al., "Human Fab Fragments Specific for the *Haemophilus influenzae* b Polysaccharide Isolated from a Bacteriophage Combinatorial Library Use Variable Region Gene Combinations and Express an Idiotype that Mirrors In Vivo Expression", Infection and Immunology, vol. 65, No. 1, pp. 261-266, (1997).
Rosen, Steven D., "Endothelial Ligands for L-Selectin", American Journal of Pathology, vol. 155, No. 4, pp. 1013-1020, (1999).
Rosen, Steve D. "Ligands for L-Selectin: Homing Inflammation, and Beyond", Annu. Rev. Immunol. vol. 22, pp. 129-156, (2004).
Schoonbroodt et al., "Oligonucleotide-Assisted Cleavage and Ligation: A Novel Directional DNA Cloning Technology to Capture cDNAs. Application in the Construction of a Human Immune Antibody Phage-display Library", Nucleic Acids Research, vol. 33, No. 9:e(81), 14 pages.
Smetsers et al., "Localization and Characterization of Melanoma-Associated Glycosaminoglycans: Differential Expression of Chondroitin and Heparin Sulfate Epitopes in Melanoma", Cancer Research, vol. 63, pp. 2965-2970, (2003).
Streeter et al., "Immunohistologic and Functional Characterization of a Vascular Addressin Involved in Lymphocyte Homing into Peripheral Lymph Nodes", The Journal of Cell Biology, vol. 107, pp. 1853-1862, (1988).
Uchimura et al., "A Major Class of L-Selectin Ligands is Eliminated in Mice Deficient in Two Sulfotransferases Expressed in High Endothelial Venules", Nature Immunology, vol. 6, No. 11, pp. 11051113, (2005).
Van De Westerlo et al., "Human Single Chain Antibodies Against Heparin: Selection, Characterization, and Effect on Coagulation", Blood, vol. 99, No. 7, pp. 2427-2433, (2002).
Van Kuppevelt et al., "Generation and Application of Type-Specific Anti-Heparan Sulfate Anitbodies Using Phage Display Technology", The Journal of Biological Chemistry, vol. 273, No. 21, pp. 12960-12966, (1998).
Van Kuppevelt et al. "Phage Display Technology to Obtain Anitheparan Sulfate Antibodies", Methods in Molecular Biology, vol. 171, Chapter 50: Phage Display Technology to Obtain Anitheparan Sulfate Antibodies, R.V. Izzo, ed., Humana Press, Totwaw, NJ, pp. 519-534, (2001).
Wang et al., "Cloning of Anti-Gal Fabs From Combinatorial Phage Display Libraries: Structural Analysis and Comparison of Fab Expression in pComb3H and pComb8 Phage", Molecular Immunology, vol. 34, No. 8/9, pp. 609-618, (1997).
Willats et al., "Cell Wall Antibodies Without Immunization: Generation and Use of De-Esterified Homogalacturonan Block-Specific Antibodies from a Naïve Phage Display Library", The Plant Journal, vol. 18, No. 1, pp. 57-65, (1999).
Zhou et al., "A Role of Midkine in the Development of the Neuromuscular Junction", Molecular and Cellular Neuroscience, vol. 10, pp. 56-70, (1997).
International Preliminary Report on Patentability dated Aug. 7, 2007 including the Written Opinion and the International Search Report dated Jan. 3, 2007 for PCT Application No. PCT/US06/03705.
International Search Report and Written Opinion dated Dec. 10, 2008 for PCT Application No. PCT/US06/03705.
Smits N. C.: "Heterogeneity of Heparan Sulfates in Human Lung", American Journal of Respiratory Cell and Molecular Biology vol. 30 2004 pp. 166-173.
Knappik A., et al.: "Fully Synthetic Human Combinatorial Antibody Libraries (HuCAL) Based on Modular Consensus Frameworks and CDRs Randomized with Trinucleotides", J. Mol. Biol. (2000) 296, 57-86.
ESR EP06734225.3, Oct. 5, 2009; 9 pages.
IPER PCT/US06/03705, Dec. 6, 2010; 9 pages.
Hemmerich s., Rosen S. 2000, GylcoBiology 10, 849-856.
Kruif Selection and Application of Human Chain scFv antibody fragments from a semi-synthetic Phage Antibody Display Library with Designed CDR3 regions, J. Mol. Biol. (1995) 248, 97-105.
Deng, S.J. Selection of antibody single-chain variable fragments with improved carbohydrate binding by phage display. J. Biol. Chem. 269, 9533 (1994).
Ravn et al. 2004, J. Mol. Biol., 343, 985-996.
ten Dam et al. 2004, J. of Biol. Chemistry, vol. 279, No. 37, pp. 38346-38352.

* cited by examiner

FIG. 3A

```
Fab Cassette of pMID21
     1                                aCAC GAGCgca
          GGATCC                           BssSI..(1/2)
          BamHI..(1/2)
    18 acgcaatTAA TGTgagttag ctcactcatt aggcacccca ggcTTTACAc tttatgcttc
        ..-35..                                            ..-10.
              Plac
    78 cggctcgtat gttgtgtgga attgtgagcg gataacaatt tc Fab cassette
BamHI Cassette: <promoter::signal::linker:-
                              ::Ckappa><VH-CH1::III-D3> trp Term
   120      acaCAGGA AACAGCTATGAC
   140 catgatta cgCCAAGCTT TGGagccttt tttttggaga ttttcaac
                  Hind3...(1/3)
             PflMI...(1/3)
signal::linker::CL
          1   2   3   4   5   6   7   8   9  10  11  12  13  14  15
         fM   K   K   T   L   L   F   A   I   P   L   V   V   P   Y
   186  gtg aaa aaa tta ttc gca att cct tta gtt gtt cct ttc tat 16  17  18  19  20
          S   H   S   A   Q
   231  tct cac aGT GCA Cag
           ApaLI........

|--------FR1-----------------------------------------> P 9D
          D   V   V   M   T   Q   S   P   L   S   L   P   V   A   P 15
          1   2   3   4   5   6   7   8   9  10  11  12  13  14
   246  gat Gtt gtg atg act cag tct cca ctc tcc ctg ccc gtc Gcc cct
```

```
            -----FR1--------->|  CDR1.............................9D
             G   E   P   A   S   I   S   C   R   S   S   R   S   L
             16  17  18  19  20  21  22  23  24  25  26  27  28  29
291          gga gag ccg gcc tcc atc tcC TGC AGg tct agt cGg agc ctc
                                         |Sse8387I|
                                         | PstI | (1/2)
                                         |  BspMI.... (1/2)

CDR1..........................|                 -----FR2------>
             L   H   R   N   G   K   T   F   F   A   W   Y   V   Q   9D
333          ctg cat agA aat gga AaG aCc tTt ttT gCt tgg tac GTG CAG
                                                           BsgI....(1/3)

------FR2-------->|
             K   P   G   Q   S   P   Q   V   L   I   Y
375          aag cca ggg cag tct cca cAG GTC CTg atc tat
                                       PpuMI....(1/2)

CDR2...........|              ------FR3---------->
             L   G   S   N   R   A   S   G   V   P   D   R   F   S   G
408          ttg ggt tct aat cgg gcc tcc gGG GTC CCt gac agg ttc agt ggc
                                             PpuMI....(2/2)

-----FR3------>
             S   E   S   G   T
453          agt gAa tca ggc aca

------FR3-------->
             D   F   T   L   K   I   S   R   V   E   A   E   D   V   G
468          gat ttT aca ctg aaa atc agc agA gtg gag gct gag gat gtt ggG ---FR3------>|  CDR3.............|
             V   Y   Y   C   M   Q   G   L   Q   T   P
513          gtt tat tac tGC ATG Caa gGT CTA Caa act cct
                                          SphI..... AccI....(1/2)
```

FIG. 3B

```
        ------- Fr4 ---------->            (SEQ ID NO:26)
       Y  T  F  G   Q   G   T   K   L   E   I   K     (SEQ ID NO:25)
546   tac act tTT GGC CAg ggg acc aag ctg gag atc aaa
                   MscI....(2/3)

VL-CL segments will be cloned in as ApaLI-AscI fragments. <-------
       Ckappa--------
       R  G  T  V   A   A   P   S   V   F   I   F   P   P   S
582   cgt gga act gtg gCT GCA Cca tct GTC TTC atc ttc ccg cca tct
                          BsgI....(2/3)   BbsI....(1/2)         Ckappa forward D  E  Q  L   K   S   G   T   A   S   V   V   C   L   L
627   gat gag cag ttg aaa tct gga act gcc tct gtt gtg tgc ctg ctg
      Ckappa forward.........

N  N  F  Y   P   R   E   A   K   V   Q   W   K   V   D
672   aat aac ttc tat ccc aga gag gcc aaa gta cag tgg aag gtg gat N  A  L  Q   S   G   N   S   Q   E   S   V   T   E   Q
717   aac gcc ctc caa tcg ggt aac tcc cag gag agt gtc aca gag cag D  S  K  D   S   T   Y   S   L   S   S   T   L   T   L
762   gac agc aag gac agc acc tac agc ctc agc agc acc ctg acG CTG
                                                              EspI....

S  K  A  D   Y   E   K   H   K   V   Y   A   C   E   V
807   AGC aaa gca gac tac gag aaa cac aaa GTC TAC gcc tgc gaa gtc
      ...EspI....                             AccI....(2/2)

T  H  Q  G   L   S   S   P   V   T   K   S   F   N   R
852   acc cat cag ggc ctg agt tcA CCG GTg aca aag agc ttc aac agg
                                AgeI....(1/2)

(SEQ ID NO:28)
       G  E  C
897   gga gag tgt taa taa
```

FIG. 3C

```
912        GG CGCGCCaatt
              AscI......
              BssHII.

924        ctatttcaag gagacagtca ta  (SEQ ID NO:27)! region upstream of Met1 preserved.

Signal for VH-CH1-IIIstump
            1   2   3   4   5   6   7   8   9  10  11  12  13  14  15
            M   K   Y   L   L   P   T   A   A   A   G   L   L   L   L
946        atg aaa tac cta ttg cct acg gca gcc gct gga ttg tta tta ctc 16  17  18  19  20  21  22
            A   A   Q   P   A   M   A
991        gcG GCC cag ccG GCC atg gcc
              SfiI.....(1/2)
                     NcoI.....

VH!
                                        FR1(DP47/V3-23)----------
                                1   2   3   4   5   6   7   8
                                E   V   Q   CAA L   TTG E   S   G
                                            |MfeI|
1012                         gaa|gtt|ctt|gtt|tta|gag|tct|ggt|

----FR1-----------------------------------                     >|...CDR1..........|---FR2----
            9  10  11  12  13  14  15  16  17  18  19  20  21  22  23    24  25  26  27  28  29  30  31  32  33  34  35  36  37  38
            G   G   L   V   Q   P   G   G   S   L   R   L   S   C   A     A   S   G   F   T   F   S   S   Y   A   M   S   W   V   R
1036       |ggc|ggt|ctt|gtt|cag|cct|ggt|ggt|tct|tta|cgt|ctt|tct|tgc|gct|

1081       |gct|TCC|GGA|ttc|act|ttc|tct|tcG|TAC|Gct|atg|tct|tgg|gtt|cgC|
              |BspEI|                            |BsiWI|                  |BstXI.
```

FIG. 3D

```
         |-----FR2-----|                                              |...CDR2...
         39  40  41  42  43  44  45  46  47  48  49  50  51  52  52a
         Q   A   P   G   K   G   L   E   W   V   S   A   I   S   G
1126    |CAa|gct|ccT|GGt|aaa|ggt|ttg|gag|tgg|gtt|tct|gct|atc|tct|ggt|
        ...BstXI

|...CDR2..........|                          |---FR3---
         53  54  55  56  57  58  59  60  61  62  63  64  65  66  67
         S   G   G   S   T   Y   Y   A   D   S   V   K   G   R   F
1171    |tct|ggt|ggc|agt|act|tac|tat|gct|gac|tcc|gtt|aaa|ggt|cgc|ttc|

|---FR3---                                                       |
         68  69  70  71  72  73  74  75  76  77  78  79  80  81  82
         T   I   S   R   D   N   S   K   N   T   L   Y   L   Q   M
1216    |act|atc|TCT|AGA|gac|aac|tct|aag|aat|act|ctc|tac|ttg|cag|atg|
                   |XbaI

|---FR3---                                          |---FR4---
         82a 82b 82c 83  84  85  86  87  88  89  90  91  92  93  94
         N   S   L   R   A   E   D   T   A   V   Y   Y   C   A   K
1261    |aac|agC|TTA|AGg|gct|gag|gac|acT|GCA|Gtc|tac|tat|tgc|gct|aaa|
               |AflII|                       |PstI|(2/2)

|.....CDR3....................|                    |---FR4---
         95  96  97  98  98a 98b 98c   99  100 101 102 103 104 105 106
         D   Y   E   G   T   G   Y       A   F   D   I   W   G   Q   G
1306    |gac|tat|gaa|ggt|act|ggt|tat|gct|ttc|gac|ATA|TGg|ggt|caa|ggt|
                                                    |NdeI|

|-----FR4------>|
         107 108 109 110 111 112 113
         T   M   V   T   V   S   S                    (SEQ ID NO:30)
1351    |act|atG|GTC|ACC|gtc|tct|agt|                 (SEQ ID NO:29)
                |BstEII|
```

FIG. 3E

```
CH1:
1372   A   S   T   K   G   P   S   V   F   P   L   A   P   S   S
       gcc tcc acc aag ggc cca tcg gtc ttc ccG CTA GCa ccc tcc tcc
                                               NheI....
       151 152 153 154 155 156 157 158 159 160 161 162 163 164 165
       K   S   T   S   G   G   T   A   A   L   G   C   L   V   K
1417   aag agc acc tct ggg ggc aca gcg gcc ctg ggc tgc ctg gtc aag
       166 167 168 169 170 171 172 173 174 175 176 177 178 179 180
       D   Y   F   P   E   P   V   T   V   S   W   N   S   G   A
1462   gac tac ttc ccc gaa ccg gtg acg gtg tcg tgg aac tca ggc gcc
       181 182 183 184 185 186 187 188 189 190 191 192 193 194 195
       L   T   S   G   V   H   T   F   P   A   V   L   Q   S   S
1507   ctg acc agc ggc gtc cac acc ttc ccg gct gtc cta cag tcc tca
       196 197 198 199 200 201 202 203 204 205 206 207 208 209 210
       G   L   Y   S   L   S   S   V   V   T   V   P   S   S   S
1552   gga ctc tac tcc ctc agc agc gta gtg acc gtg ccc tcC Agc agc
                                                          BstXI....
       211 212 213 214 215 216 217 218 219 220 221 222 223 224 225
       L   G   T   Q   T   Y   I   C   N   V   N   H   K   P   S
1597   tTG Ggc acc cag acc tac atc tgc aac gtg aat cac aag ccc agc
BstXI....
       226 227 228 229 230 231 232 233 234 235 236 237 238
       N   T   K   V   D   K   K   V   E   P   K   S   C
1642   aac acc aag gtg gac aaG AAA GTT GAG CCC AAA TCT TGT
                        His tag..........  cMyc tag......... 
       139 140 141                                               K   L   I
       A   A   A                           G   A   A   E   Q
1681   GCG GCC GCa cat cat cat cat cac cac ggg gcc gca gaa caa aaa ctc atc
       NotI......
       EagI....
```

FIG. 3F

```
            . . S   E   E   D . . L . . N . . G . . A . . A . A     E   A   S       S   A   S   N   A   S
1732 tca gaa gag gat ctg aat ggg GCC gca gaG GCt agt tct gct agt aAC GCG Tct
                                  BglI.........(3/4)                 MluI....

Domain 3 (IIIstump)------
          S   G   D   F   D   Y   E   K   M   A   N   A   N   K   G   A
1786 tcc ggt gat ttt gat tat gaa aag atg gca aac gct aat aag ggg gct M   T   E   N   A   D   E   N   A   L   Q   S   D   A   K   G
1834 atg acc gaa aat gcc gat gaa aac gcg cta cag tct gac gct aaa ggc K   L   D   S   V   A   T   D   Y   G   A   I   D   G   F
1882 aaa ctt gat tct gtc gct act gat tac ggt gct atc gat ggt ttc I   G   D   V   S   G   L   A   N   G   A   T   G   D
1930 att ggt gac gtt tcc ggc ctt gct aat ggt gct act ggt gat F   A   G   S   N   S   Q   M   A   Q   V   G   D   G   D   N
1978 ttt gct ggc tct aat tcc caa atg gct caa gtc ggt gac ggt gat aat S   P   L   M   N   N   F   R   Q   Y   L   P   S   L   P   Q
2026 tca cct tta atg aat aat ttc cgt caa tat tta cct tcc ctc cct caa S   V   E   C   R   P   F   V   F   G   A   G   K   P   Y   E
2074 tcg gtt gaa tgt cgc cct ttt gtc ttt ggc gct ggt aaa cca tat gaa F   S   I   D   C   D   K   I   N   L   F   R
2122 ttt tct att gat tgt gac aaa ata aac tta ttc cgt
                                                 End Domain 3

G   V   F   A   F   L   L   Y   V   A   T   F   M   Y   V   F140
2158 ggt gtc ttt gcg ttt ctt tta tat gtt gcc acc ttt atg tat gta ttt
     start transmembrane segment S   T   F   A   N   I   L
2206 tct acg ttt gct aac ata ctg
```

FIG. 3G

```
            R   N   K   E   S
      2227 cgt aat aag gag tct TAA
           Intracellular anchor.
```

```
           .  N   A            .
      tga aAC GCG Tga  tga GAATTC
          MluI.....       EcoRI.
```

(SEQ ID NO:32) (SEQ ID NO:31)

FIG. 3H $C_{63}H_{103}N_7O_{38}S_3$
Exact Mass: 1661.5505
Mol. Wt.: 1662.711

SEQUENCE LISTING

```
<160> NUMBER OF SEQ ID NOS: 95

<210> SEQ ID NO 1
<211> LENGTH: 6
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 1, 4, 6
<223> OTHER INFORMATION: Xaa = any amino acid
<220> FEATURE:
<221> NAME/KEY: VARIANT
<222> LOCATION: 2, 3, 5
<223> OTHER INFORMATION: Xaa = a varied or invariant basic amino acid
```

-continued

<400> SEQUENCE: 1

Xaa Xaa Xaa Xaa Xaa Xaa
 1               5

<210> SEQ ID NO 2
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 5
<223> OTHER INFORMATION: Xaa = any amino acid
<220> FEATURE:
<221> NAME/KEY: VARIANT
<222> LOCATION: 2
<223> OTHER INFORMATION: Xaa = Arg or Lys
<220> FEATURE:
<221> NAME/KEY: VARIANT
<222> LOCATION: 4
<223> OTHER INFORMATION: Xaa = Lys or Arg

<400> SEQUENCE: 2

Xaa Xaa Xaa Xaa Xaa
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly or Ser
<220> FEATURE:
<221> NAME/KEY: VARIANT
<222> LOCATION: 2, 4, 6
<223> OTHER INFORMATION: Xaa = any amino acid
<220> FEATURE:
<221> NAME/KEY: VARIANT
<222> LOCATION: 3, 5
<223> OTHER INFORMATION: Xaa = Lys or Arg

<400> SEQUENCE: 3

Xaa Xaa Xaa Xaa Xaa Xaa
 1               5

<210> SEQ ID NO 4
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 7, 8, 13, 14, 19, 20
<223> OTHER INFORMATION: n = a, g, c, or t

<400> SEQUENCE: 4
argrgtnnka rgnnkargnn k                                            21

<210> SEQ ID NO 5
<211> LENGTH: 13
<212> TYPE: PRT
<213> ORGANISM: Artificial Sequence
<220> FEATURE:
<223> OTHER INFORMATION: Synthetically generated peptide
<220> FEATURE:

```
<221> NAME/KEY: VARIANT
<222> LOCATION: 5
<223> OTHER INFORMATION: Xaa = Arg or Lys
<220> FEATURE:
<221> NAME/KEY: VARIANT
<222> LOCATION: 7, 9, 11
<223> OTHER INFORMATION: Xaa = any amino acid
<220> FEATURE:
<221> NAME/KEY: VARIANT
<222> LOCATION: 10
<223> OTHER INFORMATION: Xaa = Lys or Arg

<400> SEQUENCE: 5

Tyr Tyr Cys Ala Xaa Gly Xaa Arg Xaa Xaa Xaa Trp Gly
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 5, 8
<223> OTHER INFORMATION: Xaa = Arg or Lys
<220> FEATURE:
<221> NAME/KEY: VARIANT
<222> LOCATION: 6
<223> OTHER INFORMATION: Xaa = Gly or Ser
<220> FEATURE:
<221> NAME/KEY: VARIANT
<222> LOCATION: 7, 9, 11
<223> OTHER INFORMATION: Xaa = any amino acid
<220> FEATURE:
<221> NAME/KEY: VARIANT
<222> LOCATION: 10
<223> OTHER INFORMATION: Xaa = Lys or Arg

<400> SEQUENCE: 6

Tyr Tyr Cys Ala Xaa Xaa Xaa Xaa Xaa Xaa Xaa Trp Gly
 1               5                  10

<210> SEQ ID NO 7
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly or Ser
<220> FEATURE:
<221> NAME/KEY: VARIANT
<222> LOCATION: 2, 4, 6
<223> OTHER INFORMATION: Xaa = any amino acid
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 5
<223> OTHER INFORMATION: Xaa = Lys or Arg

<400> SEQUENCE: 7

Xaa Xaa Xaa Xaa Xaa Xaa
 1               5

<210> SEQ ID NO 8
<211> LENGTH: 18
<212> TYPE: DNA
<213> ORGANISM: Artificial Sequence
```

```
<220> FEATURE:
<223> OTHER INFORMATION: Synthetically generated oligonucleotide
<220> FEATURE:
<221> NAME/KEY: misc_feature
<222> LOCATION: 4, 5, 10, 11, 16, 17
<223> OTHER INFORMATION: n = a, g, c or t

<400> SEQUENCE: 8
rgtnnkargn nkargnnk                                              18

<210> SEQ ID NO 9
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly or Ser
<220> FEATURE:
<221> NAME/KEY: VARIANT
<222> LOCATION: 2, 4, 6
<223> OTHER INFORMATION: Xaa = any amino acid or any non-cysteine amino
      acid
<220> FEATURE:
<221> NAME/KEY: VARIANT
<222> LOCATION: 3, 5
<223> OTHER INFORMATION: Xaa = Arg or Lys

<400> SEQUENCE: 9

Xaa Xaa Xaa Xaa Xaa Xaa
 1               5

<210> SEQ ID NO 10
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 4
<223> OTHER INFORMATION: xaa = Arg or Lys
<220> FEATURE:
<221> NAME/KEY: VARIANT
<222> LOCATION: 2
<223> OTHER INFORMATION: Xaa = Gly or Ser
<220> FEATURE:
<221> NAME/KEY: VARIANT
<222> LOCATION: 3, 5, 7
<223> OTHER INFORMATION: Xaa = any amino acid
<220> FEATURE:
<221> NAME/KEY: VARIANT
<222> LOCATION: 6
<223> OTHER INFORMATION: Xaa = Lys or Arg

<400> SEQUENCE: 10

Xaa Xaa Xaa Xaa Xaa Xaa Xaa
 1               5

<210> SEQ ID NO 11
<211> LENGTH: 108
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(108)
<220> FEATURE:
<221> NAME/KEY: misc_feature
<222> LOCATION: 61, 62, 67, 68, 73, 74
<223> OTHER INFORMATION: n = a, g, c or t
```

<400> SEQUENCE: 11

```
tac ttg cag atg aac agc tta agg gct gag gac act gca gtc tac tat      48
Tyr Leu Gln Met Asn Ser Leu Arg Ala Glu Asp Thr Ala Val Tyr Tyr
  1               5                  10                  15 tgt gct arg rgt nnk arg nnk arg nnk tgg ggc caa ggt acc ctg gtc      96
Cys Ala Xaa Xaa Xaa Xaa Xaa Xaa Xaa Trp Gly Gln Gly Thr Leu Val
                 20                  25                  30 acc gtc tct agt                                                     108
Thr Val Ser Ser
         35
```

<210> SEQ ID NO 12
<211> LENGTH: 36
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 19, 22, 24
<223> OTHER INFORMATION: Xaa = Arg or Lys
<220> FEATURE:
<221> NAME/KEY: VARIANT
<222> LOCATION: 20
<223> OTHER INFORMATION: Xaa = Gly or Ser
<220> FEATURE:
<221> NAME/KEY: VARIANT
<222> LOCATION: 21, 23, 25
<223> OTHER INFORMATION: Xaa = any amino acid

<400> SEQUENCE: 12

```
Tyr Leu Gln Met Asn Ser Leu Arg Ala Glu Asp Thr Ala Val Tyr Tyr
  1               5                  10                  15

Cys Ala Xaa Xaa Xaa Xaa Xaa Xaa Xaa Trp Gly Gln Gly Thr Leu Val
                 20                  25                  30

Thr Val Ser Ser
         35
```

<210> SEQ ID NO 13
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2, 4, 6
<223> OTHER INFORMATION: Xaa = any amino acid
<220> FEATURE:
<221> NAME/KEY: VARIANT
<222> LOCATION: 5
<223> OTHER INFORMATION: Xaa = Lys or Arg

<400> SEQUENCE: 13

```
Gly Xaa Arg Xaa Xaa Xaa
  1               5
```

<210> SEQ ID NO 14
<211> LENGTH: 18
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 5, 6, 11, 12, 17, 18
<223> OTHER INFORMATION: n = a, g, c or t

<400> SEQUENCE: 14

```
ggamnncgam nnarrmnn                                              18
```

<210> SEQ ID NO 15
<211> LENGTH: 108
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(108)
<220> FEATURE:
<221> NAME/KEY: misc_feature
<222> LOCATION: 62, 63, 68, 69, 74, 75
<223> OTHER INFORMATION: n = a, c, g, or t

<400> SEQUENCE: 15

```
tac ttg cag atg aac agc tta agg gct gag gac act gca gtc tac tat      48
Tyr Leu Gln Met Asn Ser Leu Arg Ala Glu Asp Thr Ala Val Tyr Tyr
 1               5                  10                  15 tgc gct aga gga mnn cga mnn arr mnn tgg ggc caa ggt acc ctg gtc      96
Cys Ala Arg Gly Xaa Arg Xaa Xaa Xaa Trp Gly Gln Gly Thr Leu Val
             20                  25                  30 acc gtc tct agt                                                     108
Thr Val Ser Ser
         35
```

<210> SEQ ID NO 16
<211> LENGTH: 36
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 21, 23, 25
<223> OTHER INFORMATION: Xaa = any amino acid
<220> FEATURE:
<221> NAME/KEY: VARIANT
<222> LOCATION: 24
<223> OTHER INFORMATION: Xaa = Lys or Arg

<400> SEQUENCE: 16

```
Tyr Leu Gln Met Asn Ser Leu Arg Ala Glu Asp Thr Ala Val Tyr Tyr
 1               5                  10                  15

Cys Ala Arg Gly Xaa Arg Xaa Xaa Xaa Trp Gly Gln Gly Thr Leu Val
             20                  25                  30

Thr Val Ser Ser
         35
```

<210> SEQ ID NO 17
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 4, 6
<223> OTHER INFORMATION: Xaa = Arg or Lys
<220> FEATURE:
<221> NAME/KEY: VARIANT
<222> LOCATION: 2
<223> OTHER INFORMATION: Xaa = Gly or Ser
<220> FEATURE:
<221> NAME/KEY: VARIANT
<222> LOCATION: 3, 5, 7
<223> OTHER INFORMATION: Xaa = any amino acid

<400> SEQUENCE: 17

Xaa Xaa Xaa Xaa Xaa Xaa Xaa
 1               5

<210> SEQ ID NO 18
<211> LENGTH: 54
<212> TYPE: DNA
<213> ORGANISM: Artificial Sequence
<220> FEATURE:
<223> OTHER INFORMATION: Primer

<400> SEQUENCE: 18
agcacaatag tagactgcag tgtcctcagc ccttaagctg ttcatctgca agta    54

<210> SEQ ID NO 19
<211> LENGTH: 75
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 35, 36, 41, 42, 47, 48
<223> OTHER INFORMATION: n = a, c, g, or t

<400> SEQUENCE: 19
actagagacg gtgaccaggg taccttggcc ccamnncytm nncytmnnac ycytagcaca    60
atagtagact gcagt    75

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
agcggataac aatttcacac agg    23

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ccatctgatg agcagttgaa atct    24

<210> SEQ ID NO 22
<211> LENGTH: 60
<212> TYPE: DNA
<213> ORGANISM: Artificial Sequence
<220> FEATURE:
<223> OTHER INFORMATION: Primer

<400> SEQUENCE: 22
tcctctagcg caatagtaga ctgcagtgtc ctcagcccct taagctgttca tctgcaagta    60

<210> SEQ ID NO 23
<211> LENGTH: 69
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 34, 35, 40, 41, 46, 47

-continued

<223> OTHER INFORMATION: n = a, c, g, or t

<400> SEQUENCE: 23
actagagacg gtgaccaggg taccttggcc ccannkyytn nktcgnnktc ctctagcgca    60
atagtagac                                                           69

<210> SEQ ID NO 24
<211> LENGTH: 8
<212> TYPE: PRT
<213> ORGANISM: Artificial Sequence
<220> FEATURE:
<223> OTHER INFORMATION: Primer

<400> SEQUENCE: 24

Met Gln Gly Thr His Trp Pro Tyr
 1               5

<210> SEQ ID NO 25
<211> LENGTH: 581
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (186)...(581)

<400> SEQUENCE: 25
ggatccacac gagcgcaacg caattaatgt gagttagctc actcattagg caccccaggc    60
tttacacttt atgcttccgg ctcgtatgtt gtgtggaatt gtgagcggat aacaatttca   120
cacaggaaac agctatgacc atgattacgc caagctttgg agcctttttt ttggagattt   180 tcaac gtg aaa aaa tta tta ttc gca att cct tta gtt gtt cct ttc tat   230
      Met Lys Lys Leu Leu Phe Ala Ile Pro Leu Val Val Pro Phe Tyr
       1               5                  10                  15 tct cac agt gca cag gat gtt gtg atg act cag tct cca ctc tcc ctg     278
Ser His Ser Ala Gln Asp Val Val Met Thr Gln Ser Pro Leu Ser Leu
         20                  25                  30 ccc gtc gcc cct gga gag ccg gcc tcc atc tcc tgc agg tct agt cgg     326
Pro Val Ala Pro Gly Glu Pro Ala Ser Ile Ser Cys Arg Ser Ser Arg
     35                  40                  45 agc ctc ctg cat aga aat gga aag acc ttt ttt gct tgg tac gtg cag     374
Ser Leu Leu His Arg Asn Gly Lys Thr Phe Phe Ala Trp Tyr Val Gln
 50                  55                  60 aag cca ggg cag tct cca cag gtc ctg atc tat ttg ggt tct aat cgg     422
Lys Pro Gly Gln Ser Pro Gln Val Leu Ile Tyr Leu Gly Ser Asn Arg
 65                  70                  75 gcc tcc ggg gtc cct gac agg ttc agt ggc agt gaa tca ggc aca gat     470
Ala Ser Gly Val Pro Asp Arg Phe Ser Gly Ser Glu Ser Gly Thr Asp
 80                  85                  90                  95 ttt aca ctg aaa atc agc aga gtg gag gct gag gat gtt ggg gtt tat     518
Phe Thr Leu Lys Ile Ser Arg Val Glu Ala Glu Asp Val Gly Val Tyr
             100                 105                 110 tac tgc atg caa ggt cta caa act cct tac act ttt ggc cag ggg acc     566
Tyr Cys Met Gln Gly Leu Gln Thr Pro Tyr Thr Phe Gly Gln Gly Thr
         115                 120                 125 aag ctg gag atc aaa                                                 581
Lys Leu Glu Ile Lys
         130

<210> SEQ ID NO 26
<211> LENGTH: 132
<212> TYPE: PRT

<213> ORGANISM: Artificial Sequence
<220> FEATURE:
<223> OTHER INFORMATION: Synthetically generated peptide

<400> SEQUENCE: 26

```
Met Lys Lys Leu Leu Phe Ala Ile Pro Leu Val Val Pro Phe Tyr Ser
 1               5                  10                  15

His Ser Ala Gln Asp Val Val Met Thr Gln Ser Pro Leu Ser Leu Pro
            20                  25                  30

Val Ala Pro Gly Glu Pro Ala Ser Ile Ser Cys Arg Ser Ser Arg Ser
        35                  40                  45

Leu Leu His Arg Asn Gly Lys Thr Phe Phe Ala Trp Tyr Val Gln Lys
    50                  55                  60

Pro Gly Gln Ser Pro Gln Val Leu Ile Tyr Leu Gly Ser Asn Arg Ala
65                  70                  75                  80

Ser Gly Val Pro Asp Arg Phe Ser Gly Ser Glu Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Gly Leu Gln Thr Pro Tyr Thr Phe Gly Gln Gly Thr Lys
        115                 120                 125

Leu Glu Ile Lys
    130
```

<210> SEQ ID NO 27
<211> LENGTH: 364
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(324)

<400> SEQUENCE: 27

```
cgt gga act gtg gct gca cca tct gtc ttc atc ttc ccg cca tct gat     48
Arg Gly Thr Val Ala Ala Pro Ser Val Phe Ile Phe Pro Pro Ser Asp
 1               5                  10                  15 gag cag ttg aaa tct gga act gcc tct gtt gtg tgc ctg ctg aat aac     96
Glu Gln Leu Lys Ser Gly Thr Ala Ser Val Val Cys Leu Leu Asn Asn
            20                  25                  30 ttc tat ccc aga gag gcc aaa gta cag tgg aag gtg gat aac gcc ctc    144
Phe Tyr Pro Arg Glu Ala Lys Val Gln Trp Lys Val Asp Asn Ala Leu
        35                  40                  45 caa tcg ggt aac tcc cag gag agt gtc aca gag cag gac agc aag gac    192
Gln Ser Gly Asn Ser Gln Glu Ser Val Thr Glu Gln Asp Ser Lys Asp
    50                  55                  60 agc acc tac agc ctc agc agc acc ctg acg ctg agc aaa gca gac tac    240
Ser Thr Tyr Ser Leu Ser Ser Thr Leu Thr Leu Ser Lys Ala Asp Tyr
65                  70                  75                  80 gag aaa cac aaa gtc tac gcc tgc gaa gtc acc cat cag ggc ctg agt    288
Glu Lys His Lys Val Tyr Ala Cys Glu Val Thr His Gln Gly Leu Ser
                85                  90                  95 tca ccg gtg aca aag agc ttc aac agg gga gag tgt taataaggcg         334
Ser Pro Val Thr Lys Ser Phe Asn Arg Gly Glu Cys
            100                 105 cgccaattct atttcaagga gacagtcata                                   364
```

<210> SEQ ID NO 28
<211> LENGTH: 108
<212> TYPE: PRT

```
<213> ORGANISM: Artificial Sequence
<220> FEATURE:
<223> OTHER INFORMATION: Synthetically generated peptide

<400> SEQUENCE: 28

Arg Gly Thr Val Ala Ala Pro Ser Val Phe Ile Phe Pro Pro Ser Asp
 1               5                  10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 29
<211> LENGTH: 426
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(426)

<400> SEQUENCE: 29 atg aaa tac cta ttg cct acg gca gcc gct gga ttg tta tta ctc gcg    48
Met Lys Tyr Leu Leu Pro Thr Ala Ala Ala Gly Leu Leu Leu Leu Ala
 1               5                  10                  15 gcc cag ccg gcc atg gcc gaa gtt caa ttg tta gag tct ggt ggc ggt    96
Ala Gln Pro Ala Met Ala Glu Val Gln Leu Leu Glu Ser Gly Gly Gly
            20                  25                  30 ctt gtt cag cct ggt ggt tct tta cgt ctt tct tgc gct gct tcc gga   144
Leu Val Gln Pro Gly Gly Ser Leu Arg Leu Ser Cys Ala Ala Ser Gly
        35                  40                  45 ttc act ttc tct tcg tac gct atg tct tgg gtt cgc caa gct cct ggt   192
Phe Thr Phe Ser Ser Tyr Ala Met Ser Trp Val Arg Gln Ala Pro Gly
    50                  55                  60 aaa ggt ttg gag tgg gtt tct gct atc tct ggt tct ggt ggc agt act   240
Lys Gly Leu Glu Trp Val Ser Ala Ile Ser Gly Ser Gly Gly Ser Thr
65                  70                  75                  80 tac tat gct gac tcc gtt aaa ggt cgc ttc act atc tct aga gac aac   288
Tyr Tyr Ala Asp Ser Val Lys Gly Arg Phe Thr Ile Ser Arg Asp Asn
                85                  90                  95 tct aag aat act ctc tac ttg cag atg aac agc tta agg gct gag gac   336
Ser Lys Asn Thr Leu Tyr Leu Gln Met Asn Ser Leu Arg Ala Glu Asp
            100                 105                 110 act gca gtc tac tat tgc gct aaa gac tat gaa ggt act ggt tat gct   384
Thr Ala Val Tyr Tyr Cys Ala Lys Asp Tyr Glu Gly Thr Gly Tyr Ala
        115                 120                 125 ttc gac ata tgg ggt caa ggt act atg gtc acc gtc tct agt           426
Phe Asp Ile Trp Gly Gln Gly Thr Met Val Thr Val Ser Ser
    130                 135                 140

<210> SEQ ID NO 30
<211> LENGTH: 142
<212> TYPE: PRT
```

-continued

```
<213> ORGANISM: Artificial Sequence
<220> FEATURE:
<223> OTHER INFORMATION: Synthetically generated peptide

<400> SEQUENCE: 30

Met Lys Tyr Leu Leu Pro Thr Ala Ala Ala Gly Leu Leu Leu Leu Ala
 1               5                  10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
         35                  40                  45

Phe Thr Phe Ser Ser Tyr Ala Met Ser Trp Val Arg Gln Ala Pro Gly
     50                  55                  60

Lys Gly Leu Glu Trp Val Ser Ala Ile Ser Gly Ser Gly Gly Ser Thr
 65                  70                  75                  80

Tyr Tyr Ala Asp Ser Val Lys Gly Arg Phe Thr Ile Ser Arg Asp Asn
                 85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Asp Tyr Glu Gly Thr Gly Tyr Ala
        115                 120                 125

Phe Asp Ile Trp Gly Gln Gly Thr Met Val Thr Val Ser Ser
    130                 135                 140

<210> SEQ ID NO 31
<211> LENGTH: 894
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(894)

<400> SEQUENCE: 31 gcc tcc acc aag ggc cca tcg gtc ttc ccg cta gca ccc tcc tcc aag      48
Ala Ser Thr Lys Gly Pro Ser Val Phe Pro Leu Ala Pro Ser Ser Lys
 1               5                  10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
         35                  40                  45 ggc gtc cac acc ttc ccg gct gtc cta cag tcc tca gga ctc tac tcc     192
Gly Val His Thr Phe Pro Ala Val Leu Gln Ser Ser Gly Leu Tyr Ser
     50                  55                  60 ctc agc agc gta gtg acc gtg ccc tcc agc agc ttg ggc acc cag acc     240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                 85                  90                  95 aaa gtt gag ccc aaa tct tgt gcg gcc gca cat cat cat cac cat cac     336
Lys Val Glu Pro Lys Ser Cys Ala Ala Ala His His His His His His
            100                 105                 110 ggg gcc gca gaa caa aaa ctc atc tca gaa gag gat ctg aat ggg gcc     384
Gly Ala Ala Glu Gln Lys Leu Ile Ser Glu Glu Asp Leu Asn Gly Ala
        115                 120                 125 gca gag gct agt tct gct agt aac gcg tct tcc ggt gat ttt gat tat     432
Ala Glu Ala Ser Ser Ala Ser Asn Ala Ser Ser Gly Asp Phe Asp Tyr
```

```
                130                 135                 140
gaa aag atg gca aac gct aat aag ggg gct atg acc gaa aat gcc gat         480
Glu Lys Met Ala Asn Ala Asn Lys Gly Ala Met Thr Glu Asn Ala Asp
145                 150                 155                 160 gaa aac gcg cta cag tct gac gct aaa ggc aaa ctt gat tct gtc gct         528
Glu Asn Ala Leu Gln Ser Asp Ala Lys Gly Lys Leu Asp Ser Val Ala
                165                 170                 175 act gat tac ggt gct gct atc gat ggt ttc att ggt gac gtt tcc ggc         576
Thr Asp Tyr Gly Ala Ala Ile Asp Gly Phe Ile Gly Asp Val Ser Gly
            180                 185                 190 ctt gct aat ggt aat ggt gct act ggt gat ttt gct ggc tct aat tcc         624
Leu Ala Asn Gly Asn Gly Ala Thr Gly Asp Phe Ala Gly Ser Asn Ser
        195                 200                 205 caa atg gct caa gtc ggt gac ggt gat aat tca cct tta atg aat aat         672
Gln Met Ala Gln Val Gly Asp Gly Asp Asn Ser Pro Leu Met Asn Asn
    210                 215                 220 ttc cgt caa tat tta cct tcc ctc cct caa tcg gtt gaa tgt cgc cct         720
Phe Arg Gln Tyr Leu Pro Ser Leu Pro Gln Ser Val Glu Cys Arg Pro
225                 230                 235                 240 ttt gtc ttt ggc gct ggt aaa cca tat gaa ttt tct att gat tgt gac         768
Phe Val Phe Gly Ala Gly Lys Pro Tyr Glu Phe Ser Ile Asp Cys Asp
                245                 250                 255 aaa ata aac tta ttc cgt ggt gtc ttt gcg ttt ctt tta tat gtt gcc         816
Lys Ile Asn Leu Phe Arg Gly Val Phe Ala Phe Leu Leu Tyr Val Ala
            260                 265                 270 acc ttt atg tat gta ttt tct acg ttt gct aac ata ctg cgt aat aag         864
Thr Phe Met Tyr Val Phe Ser Thr Phe Ala Asn Ile Leu Arg Asn Lys
        275                 280                 285 gag tct taa tga aac gcg tga tga gaa ttc                                 894
Glu Ser  *   *  Asn Ala  *   *  Glu Phe
    290

<210> SEQ ID NO 32
<211> LENGTH: 292
<212> TYPE: PRT
<213> ORGANISM: Artificial Sequence
<220> FEATURE:
<223> OTHER INFORMATION: Synthetically generated peptide

<400> SEQUENCE: 32

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Ala Ala Ala His His His His His His
            100                 105                 110

Gly Ala Ala Glu Gln Lys Leu Ile Ser Glu Glu Asp Leu Asn Gly Ala
        115                 120                 125

Ala Glu Ala Ser Ser Ala Ser Asn Ala Ser Ser Gly Asp Phe Asp Tyr
    130                 135                 140

Glu Lys Met Ala Asn Ala Asn Lys Gly Ala Met Thr Glu Asn Ala Asp
```

```
                145                 150                 155                 160
Glu Asn Ala Leu Gln Ser Asp Ala Lys Gly Lys Leu Asp Ser Val Ala
                    165                 170                 175

Thr Asp Tyr Gly Ala Ala Ile Asp Gly Phe Ile Gly Asp Val Ser Gly
            180                 185                 190

Leu Ala Asn Gly Asn Gly Ala Thr Gly Asp Phe Ala Gly Ser Asn Ser
                195                 200                 205

Gln Met Ala Gln Val Gly Asp Gly Asp Asn Ser Pro Leu Met Asn Asn
            210                 215                 220

Phe Arg Gln Tyr Leu Pro Ser Leu Pro Gln Ser Val Glu Cys Arg Pro
225                 230                 235                 240

Phe Val Phe Gly Ala Gly Lys Pro Tyr Glu Phe Ser Ile Asp Cys Asp
                245                 250                 255

Lys Ile Asn Leu Phe Arg Gly Val Phe Ala Phe Leu Leu Tyr Val Ala
                260                 265                 270

Thr Phe Met Tyr Val Phe Ser Thr Phe Ala Asn Ile Leu Arg Asn Lys
                275                 280                 285

Glu Ser Asn Ala
        290

<210> SEQ ID NO 33
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Ala Trp Val Arg Gln Ala Pro Gly Lys Gly Leu Glu Trp Val
        35                  40                  45

Ser Ser Ile Ser Ser Ser Gly Gly His Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Arg Lys Arg Asn Arg Asn
            100

<210> SEQ ID NO 34
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 34

Gln Asp Ile Gln Met Thr Gln Ser Pro Asp Ser Leu Ala Val Ser Leu
1               5                   10                  15

Gly Glu Arg Ala Thr Ile Asn Cys Lys Ser Ser Gln Ser Val Lys Ser
            20                  25                  30

Asn Asn Lys Asn Tyr Leu Ala Trp Tyr Gln Gln Lys Pro Gly Gln Pro
        35                  40                  45

Pro Lys Leu Leu Ile Tyr Trp Ala Ser Thr Arg Glu Ser Gly Val Pro
```

```
                  50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Gln Gln Tyr
                 85                  90                  95

Tyr Ser Thr Pro Pro Thr
            100

<210> SEQ ID NO 35
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 35

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
             20                  25                  30

Arg Met Asn Trp Val Arg Gln Ala Pro Gly Lys Gly Leu Glu Trp Val
         35                  40                  45

Ser Ser Ile Gly Ser Ser Gly Gly His Thr Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Arg Lys Arg Asn Arg Thr
            100

<210> SEQ ID NO 36
<211> LENGTH: 99
<212> TYPE: PRT
<213> ORGANISM: Artificial Sequence
<220> FEATURE:
<223> OTHER INFORMATION: Synthetically generated peptide

<400> SEQUENCE: 36

Gln Asp Ile Gln Met Thr Gln Ser Pro Gly Thr Leu Ser Leu Ser Pro
  1               5                  10                  15

Gly Glu Arg Ala Thr Leu Ser Cys Arg Ala Ser Gln Ser Val Ser Ser
             20                  25                  30

Ser Tyr Leu Ala Trp Tyr Gln Gln Lys Pro Gly Gln Ala Pro Arg Leu
         35                  40                  45

Leu Ile Tyr Gly Ala Ser Ser Arg Ala Thr Gly Ile Pro Asp Arg Phe
 50                  55                  60

Ser Gly Ser Gly Ser Gly Thr Asp Phe Thr Leu Thr Ile Ser Arg Leu
 65                  70                  75                  80

Glu Pro Glu Asp Phe Ala Val Tyr Tyr Cys Gln Gln Tyr Gly Ser Ser
                 85                  90                  95

Pro Arg Thr

<210> SEQ ID NO 37
<211> LENGTH: 102
<212> TYPE: PRT
<213> ORGANISM: Artificial Sequence
<220> FEATURE:
<223> OTHER INFORMATION: Synthetically generated peptide
```

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ile Met Ser Trp Val Arg Gln Ala Pro Gly Lys Gly Leu Glu Trp Val
        35                  40                  45

Ser Tyr Ile Ser Pro Ser Gly Thr Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Arg Arg Arg Thr Lys His
            100

<210> SEQ ID NO 38
<211> LENGTH: 103
<212> TYPE: PRT
<213> ORGANISM: Artificial Sequence
<220> FEATURE:
<223> OTHER INFORMATION: Synthetically generated peptide

<400> SEQUENCE: 38

Gln Asp Ile Gln Met Thr Gln Ser Pro Leu Ser Leu Pro Val Thr Leu
1               5                   10                  15

Gly Gln Ser Ala Ser Ile Ser Cys Arg Ser Ser Gln Ser Leu Val His
            20                  25                  30

Ser Asp Gly Asn Thr Tyr Leu Asn Trp Phe Gln Gln Arg Pro Gly Gln
        35                  40                  45

Ser Pro Arg Arg Leu Ile Tyr Lys Val Ser Asn Arg Asp Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Trp Pro Tyr Thr
            100

<210> SEQ ID NO 39
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 39

Asn Tyr Thr Met Ala
1               5

<210> SEQ ID NO 40
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 40

Ser Ile Ser Ser Ser Gly Gly His Thr Pro Tyr Ala Asp Ser Val Lys
1               5                   10                  15

Gly

<210> SEQ ID NO 41
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 41

Gly Lys Arg Asn Arg Asn
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 42

Gly Tyr Arg Met Asn
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 43

Ser Ile Gly Ser Ser Gly Gly His Thr Ser Tyr Ala Asp Ser Val Lys
1               5                   10                  15

Gly

<210> SEQ ID NO 44
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 44

Gly Lys Arg Asn Arg Thr
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 45

Glu Tyr Ile Met Ser
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 46

Tyr Ile Ser Pro Ser Gly Gly Thr Thr Lys Tyr Ala Asp Ser Val Lys

```
                1               5                  10                 15

Gly

<210> SEQ ID NO 47
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 47

Gly Arg Arg Thr Lys His
1               5

<210> SEQ ID NO 48
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 48

Lys Ser Ser Gln Ser Val Lys Ser Asn Asn Lys Asn Tyr Leu Ala
1               5                  10                 15

<210> SEQ ID NO 49
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 49

Trp Ala Ser Thr Arg Glu Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 50

Gln Gln Tyr Tyr Ser Thr Pro Pro Thr
1               5

<210> SEQ ID NO 51
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 51

Arg Ala Ser Gln Ser Val Ser Ser Ser Tyr Leu Ala
1               5                  10

<210> SEQ ID NO 52
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 52

Gly Ala Ser Ser Arg Ala Thr
```

<210> SEQ ID NO 53
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 53

Gln Gln Tyr Gly Ser Ser Pro Arg Thr
1               5

<210> SEQ ID NO 54
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 54

Arg Ser Ser Gln Ser Leu Val His Ser Asp Gly Asn Thr Tyr Leu Asn
1               5                   10                  15

<210> SEQ ID NO 55
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 55

Lys Val Ser Asn Arg Asp Ser
1               5

<210> SEQ ID NO 56
<211> LENGTH: 333
<212> TYPE: DNA
<213> ORGANISM: Artificial Sequence
<220> FEATURE:
<223> OTHER INFORMATION: Synthetically generated oligonucleotide

<400> SEQUENCE: 56
cagagcgtct tgactcagcc acccucagtg tcagtggccc caggaaggac ggccaccatt      60
acctgtgggg gaaaaaacat tggagctaaa agtgtcaact ggtaccaaca gaggccaggc     120
caggcccctg tcctggtcat cttctatgat accgaccggc cgcaggaat aactgggcga      180 ttgtctggct ccaattctgg gaactcggcc accctgacca tcagcagggt cgaggccggg     240
gacgaggccg attattactg tcaggtgtgg ggtgtcagtg gtgatcatcc ggttttcggc     300
ggagggacta ggctgaccgt cctgggtcag ccc                                  333

<210> SEQ ID NO 57
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 57

Gln Ser Val Leu Thr Gln Pro Pro Ser Val Ser Val Ala Pro Gly Arg
1               5                   10                  15

Thr Ala Thr Ile Thr Cys Gly Gly Lys Asn Ile Gly Ala Lys Ser Val
                20                  25                  30

Asn Trp Tyr Gln Gln Arg Pro Gly Gln Ala Pro Val Leu Val Ile Phe

```
                35                  40                  45
Tyr Asp Thr Asp Arg Pro Ala Gly Ile Thr Gly Arg Leu Ser Gly Ser
 50                  55                  60

Asn Ser Gly Asn Ser Ala Thr Leu Thr Ile Ser Arg Val Glu Ala Gly
 65                  70                  75                  80

Asp Glu Ala Asp Tyr Tyr Cys Gln Val Trp Gly Val Ser Gly Asp His
                 85                  90                  95

Pro Val Phe Gly Gly Gly Thr Arg Leu Thr Val Leu Gly Gln Pro
            100                 105                 110
```

<210> SEQ ID NO 58
<211> LENGTH: 312
<212> TYPE: DNA
<213> ORGANISM: Artificial Sequence
<220> FEATURE:
<223> OTHER INFORMATION: Synthetically generated oligonucleotide

<400> SEQUENCE: 58

```
gaagttcaat tgttagagtc tggtggcggt cttgttcagc ctggtggttc tttacgtctt    60
tcttgcgctg cttccggatt cactttctct ggttacatga tggcttgggt tcgccaagct   120
cctggtaaag gtttggagtg ggtttcttgg atctctcctt ctggtggctt tactaagtat   180
gctgactccg ttaaaggtcg cttcactatc tctagagaca actctaagaa tactctctac   240
ttgcagatga acagcttaag ggctgaggac actgcagtct actattgcgc tagaggaagc   300
cgactcaggc at                                                      312
```

<210> SEQ ID NO 59
<211> LENGTH: 104
<212> TYPE: PRT
<213> ORGANISM: Artificial Sequence
<220> FEATURE:
<223> OTHER INFORMATION: Synthetically generated peptide

<400> SEQUENCE: 59

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
             20                  25                  30

Met Met Ala Trp Val Arg Gln Ala Pro Gly Lys Gly Leu Glu Trp Val
         35                  40                  45

Ser Trp Ile Ser Pro Ser Gly Gly Phe Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Arg Leu Arg His
            100
```

<210> SEQ ID NO 60
<211> LENGTH: 326
<212> TYPE: DNA
<213> ORGANISM: Artificial Sequence
<220> FEATURE:
<223> OTHER INFORMATION: Synthetically generated oligonucleotide

<400> SEQUENCE: 60

```
caagacatcc agatgaccca gtctccatcc tccctgtctg catctgtagg agacagagtc    60
accatcactt gccgggcaag tcagggcatt agaaatgatt taggctggta tcagcagaaa   120
```

```
ccagggaaag cccctaagcg cctgatctat gctgcatcca gtttgcaaag tggggtccca    180
tcaaggttca gcggcagtgg atctgggaca gaattcactc tcacaatcag cagcctgcag    240
cctgaagatt ttgcaactta ttactgtcta cagcataata gttacccgta cacttttggc    300
caggggacca agctggagat caaacg                                         326
```

```
<210> SEQ ID NO 61
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 61
```

| Gln | Asp | Ile | Gln | Met | Thr | Gln | Ser | Pro | Ser | Leu | Ser | Ala | Ser | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gly | Asp | Arg | Val | Thr | Ile | Thr | Cys | Arg | Ala | Ser | Gln | Gly | Ile | Arg | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Leu | Gly | Trp | Tyr | Gln | Gln | Lys | Pro | Gly | Lys | Ala | Pro | Lys | Arg | Leu |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Ile | Tyr | Ala | Ala | Ser | Ser | Leu | Gln | Ser | Gly | Val | Pro | Ser | Arg | Phe | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Ser | Gly | Ser | Gly | Thr | Glu | Phe | Thr | Leu | Thr | Ile | Ser | Ser | Leu | Gln |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Pro | Glu | Asp | Phe | Ala | Thr | Tyr | Tyr | Cys | Leu | Gln | His | Asn | Ser | Tyr | Pro |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Thr | Phe | Gly | Gln | Gly | Thr | Lys | Leu | Glu | Ile | Lys |
|-----|-----|-----|-----|-----|-----|-----|-----|-----|-----|-----|-----|
|     |     |     | 100 |     |     |     |     | 105 |     |     |     |

```
<210> SEQ ID NO 62
<211> LENGTH: 312
<212> TYPE: DNA
<213> ORGANISM: Artificial Sequence
<220> FEATURE:
<223> OTHER INFORMATION: Synthetically generated oligonucleotide

<400> SEQUENCE: 62
gaagttcaat tgttagagtc tggtggcggt cttgttcagc ctggtggttc tttacgtctt     60
tcttgcgctg cttccggatt cactttctct ggttacatga tgcagtgggt tcgccaagct    120
cctggtaaag gtttggagtg ggttcttcct atctctcctt ctggtggctt tactgagtat    180
gctgactccg ttaaaggtcg cttcactatc tctagagaca actctaagaa tactctctac    240
ttgcagatga acagcttaag ggctgaggac actgcagtct actattgcgc tagaggacgg    300
cgacacagga at                                                        312
```

```
<210> SEQ ID NO 63
<211> LENGTH: 104
<212> TYPE: PRT
<213> ORGANISM: Artificial Sequence
<220> FEATURE:
<223> OTHER INFORMATION: Synthetically generated peptide

<400> SEQUENCE: 63
```

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Gly | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Met | Met | Gln | Trp | Val | Arg | Gln | Ala | Pro | Gly | Lys | Gly | Leu | Glu | Trp | Val |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

```
Ser Ser Ile Ser Pro Ser Gly Gly Phe Thr Glu Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Arg Arg His Arg Asn
            100
```

<210> SEQ ID NO 64
<211> LENGTH: 330
<212> TYPE: DNA
<213> ORGANISM: Artificial Sequence
<220> FEATURE:
<223> OTHER INFORMATION: Synthetically generated oligonucleotide

<400> SEQUENCE: 64

```
caagacatcc atatgaccca gtctccaggc accctgtctt tgtctccagg ggaaagagcc    60
accctctcct gcagggccag tcagagtatt agcaacacct acttagcctg gtaccagcag   120
aaacctggcc aggctcccag gctcctcatc tatggtgcat ccagcagggc cactggcatc   180
ccagacaggt tcagtggcag tgggtctggg acagacttca ctctcaccat cagcaggctg   240
gagcctgaag attttgcagt gtattactgt cagcagtatg gtagctcacc cctgtacact   300
tttggccagg ggaccaagtt ggagatcaaa                                    330
```

<210> SEQ ID NO 65
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 65

```
Gln Asp Ile His Met Thr Gln Ser Pro Gly Thr Leu Ser Leu Ser Pro
  1               5                  10                  15
Gly Glu Arg Ala Thr Leu Ser Cys Arg Ala Ser Gln Ser Ile Ser Asn
                 20                  25                  30
Thr Tyr Leu Ala Trp Tyr Gln Gln Lys Pro Gly Gln Ala Pro Arg Leu
            35                  40                  45
Leu Ile Tyr Gly Ala Ser Ser Arg Ala Thr Gly Ile Pro Asp Arg Phe
 50                  55                  60
Ser Gly Ser Gly Ser Gly Thr Asp Phe Thr Leu Thr Ile Ser Arg Leu
 65                  70                  75                  80
Glu Pro Glu Asp Phe Ala Val Tyr Tyr Cys Gln Gln Tyr Gly Ser Ser
                 85                  90                  95
Pro Leu Tyr Thr Phe Gly Gln Gly Thr Lys Leu Glu Ile Lys
            100                 105                 110
```

<210> SEQ ID NO 66
<211> LENGTH: 312
<212> TYPE: DNA
<213> ORGANISM: Artificial Sequence
<220> FEATURE:
<223> OTHER INFORMATION: Synthetically generated oligonucleotide

<400> SEQUENCE: 66

```
gaagttcaat tgttagagtc tggtggcggt cttgttcagc ctggtggttc tttacgtctt    60
tcttgcgctg cttccggatt cactttctct ggttacatga tgaattgggt tcgccaagct   120
```

```
cctggtaaag gtttggagtg ggtttcttct atcggtcctt ctggtggcta tactacttat    180
gctgactccg ttaaaggtca cttcactatc tctagagaca actctaagaa cactctctac    240
ttgcagatga acagcttaag ggctgaggac actgcagtct actattgcgc tagaggactg    300
cgaatgaaaa ag                                                        312
```

```
<210> SEQ ID NO 67
<211> LENGTH: 104
<212> TYPE: PRT
<213> ORGANISM: Artificial Sequence
<220> FEATURE:
<223> OTHER INFORMATION: Synthetically generated peptide

<400> SEQUENCE: 67
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Met Met Asn Trp Val Arg Gln Ala Pro Gly Lys Gly Leu Glu Trp Val
        35                  40                  45

Ser Ser Ile Gly Pro Ser Gly Gly Tyr Thr Thr Tyr Ala Asp Ser Val
    50                  55                  60

Lys Gly His Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Arg Met Lys Lys
            100

```
<210> SEQ ID NO 68
<211> LENGTH: 336
<212> TYPE: DNA
<213> ORGANISM: Artificial Sequence
<220> FEATURE:
<223> OTHER INFORMATION: Synthetically generated oligonucleotide

<400> SEQUENCE: 68
cagagcgtct tgactcagga ccctgctgtg tctgtggcct tgggacagac agtcaggatc     60
acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactggggc tcaggcggaa    240
gatgaggctg actattactg taactcccgg gacagcagtg gtaacatctg gaaggtattc    300
ggcggaggga ccaagctgac cgtcctaggt cagccc                             336
```

```
<210> SEQ ID NO 69
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 69
```

Gln Ser Val Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

-continued

```
Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Ile
                 85                  90                  95

Trp Lys Val Phe Gly Gly Gly Thr Lys Leu Thr Val Leu Gly Gln Pro
            100                 105                 110
```

<210> SEQ ID NO 70
<211> LENGTH: 312
<212> TYPE: DNA
<213> ORGANISM: Artificial Sequence
<220> FEATURE:
<223> OTHER INFORMATION: Synthetically generated oligonucleotide

<400> SEQUENCE: 70

```
gaagttcaat tgttagagtc tggtggcggt cttgttcagc ctggtggttc tttacgtctt      60
tcttgcgctg cttccggatt cactttctct gtttacccta tgcattgggt tcgccaagct     120
cctggtaaag gtttggagtg gtttcttat atcggttctt ctggtggcga gactatgtat      180
gctgactccg ttaaaggtcg cttcactatc tctagagaca actctaagaa tactctctac     240
ttgcagatga acagcttaag ggctgaggac actgcagtct actattgcgc tagaggaaaa     300
cgaaacaaaa ga                                                         312
```

<210> SEQ ID NO 71
<211> LENGTH: 104
<212> TYPE: PRT
<213> ORGANISM: Artificial Sequence
<220> FEATURE:
<223> OTHER INFORMATION: Synthetically generated peptide

<400> SEQUENCE: 71

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Val Tyr
             20                  25                  30

Pro Met His Trp Val Arg Gln Ala Pro Gly Lys Gly Leu Glu Trp Val
         35                  40                  45

Ser Tyr Ile Gly Ser Ser Gly Gly Glu Thr Met Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Arg Asn Lys Arg
            100
```

<210> SEQ ID NO 72
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 72

```
Gly Gly Lys Asn Ile Gly Ala Lys Ser Val Asn
  1               5                  10
```

<210> SEQ ID NO 73

```
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 73

Arg Ala Ser Gln Gly Ile Arg Asn Asp Leu Gly
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 74

Arg Ala Ser Gln Ser Ile Ser Asn Thr Tyr Leu Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 75

Gln Gly Asp Ser Leu Arg Ser Tyr Tyr Ala Ser
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 76

Tyr Asp Thr Asp Arg Pro Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 77

Ala Ala Ser Ser Leu Gln Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 78

Gly Ala Ser Ser Arg Ala Thr
1               5

<210> SEQ ID NO 79
<211> LENGTH: 7
<212> TYPE: PRT
```

```
<213> ORGANISM: Artificial Sequence
<220> FEATURE:
<223> OTHER INFORMATION: Synthetically generated peptide

<400> SEQUENCE: 79

Gly Lys Asn Asn Arg Pro Ser
1               5

<210> SEQ ID NO 80
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 80

Gln Val Trp Gly Val Ser Gly Asp His Pro Val
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 81

Leu Gln His Asn Ser Tyr Pro Tyr Thr
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 82

Gln Gln Tyr Gly Ser Ser Pro Leu Tyr Thr
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 83

Asn Ser Arg Asp Ser Ser Gly Asn Ile Trp Lys Val
1               5                   10

<210> SEQ ID NO 84
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 84

Gly Tyr Met Met Ala
1               5

<210> SEQ ID NO 85
<211> LENGTH: 5
<212> TYPE: PRT
<213> ORGANISM: Artificial Sequence
<220> FEATURE:
```

-continued

```
<223> OTHER INFORMATION: Synthetically generated peptide

<400> SEQUENCE: 85

Gly Tyr Met Met Gln
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 86

Gly Tyr Met Met Asn
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 87

Val Tyr Pro Met His
1               5

<210> SEQ ID NO 88
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 88

Trp Ile Ser Pro Ser Gly Gly Phe Thr Lys Tyr Ala Asp Ser Val Lys
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 89

Ser Ile Ser Pro Ser Gly Gly Phe Thr Glu Tyr Ala Asp Ser Val Lys
1               5                   10                  15

Gly

<210> SEQ ID NO 90
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 90

Ser Ile Gly Pro Ser Gly Gly Tyr Thr Thr Tyr Ala Asp Ser Val Lys
1               5                   10                  15

Gly

<210> SEQ ID NO 91
```

```
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 91

Tyr Ile Gly Ser Ser Gly Gly Glu Thr Met Tyr Ala Asp Ser Val Lys
 1               5                  10                  15
Gly

<210> SEQ ID NO 92
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 92

Gly Ser Arg Leu Arg His
 1               5

<210> SEQ ID NO 93
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 93

Gly Arg Arg His Arg Asn
 1               5

<210> SEQ ID NO 94
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 94

Gly Leu Arg Met Lys Lys
 1               5

<210> SEQ ID NO 95
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 95

Gly Lys Arg Asn Lys Arg
 1               5
```

LIBRARIES AND METHODS FOR ISOLATING ANTIBODIES

CROSS-REFERENCE TO RELATED APPLICATIONS

This application claims priority to U.S. Application Ser. No. 60/649,065, filed on Feb. 1, 2005, the contents of which are hereby incorporated by reference.

BACKGROUND

This application relates to identifying antibodies that bind to a carbohydrate moiety.

It has been reported that it is difficult to raise antibodies to polysaccharides and molecules such as heparan sulfate by conventional immunization. There are, however, several disease states in which sulfated carbohydrates are found.

SUMMARY

In one aspect, the disclosure features a method for identifying an antibody that binds to a carbohydrate moiety. The method includes: providing a protein library that includes a plurality of diverse antibodies, each antibody including a heavy chain variable domain sequence and/or a light chain variable domain sequence, contacting members of the protein library to a target molecule that includes a carbohydrate moiety; and identifying one or more members that interact with the target molecule. The method can be used to identify an antibody to an epitope that includes a negatively charged carbohydrate moiety and may further include confirming that the antibody interacts with (e.g., binds to) the target molecule and/or epitope.

In one embodiment, the heavy chain variable domain sequence includes diversity in HC CDR3, but at least one or two amino acid positions are restricted to a basic amino acid. Restricted positions can be, independently, completely invariant, or can be allowed to vary among basic amino acids. For example, one basic amino acid position is an invariant arginine, and another basic amino acid position is allowed to vary between arginine and lysine. At least two of the basic amino acid positions can be separated by at least one amino acid position that is allowed to vary among at least ten different amino acids. For example, for each antibody of the plurality, HC CDR3 includes X-B-B-X-B-X (SEQ ID NO:1) (wherein B is a varied or invariant basic amino acid); or X-(R/K)-X-(K/R)-X (SEQ ID NO:2); or (G/S)-X-(K/R)-X-(K/R)-X (SEQ ID NO:3). In one embodiment, X is any amino acid. In another embodiment, X represents positions that are varied among at least two, three, four, five, six, ten, twelve, thirteen, fifteen, sixteen, or nineteen different amino-acid types. For example, X can represent, independently, a position that is varied among non-cysteine amino acids (e.g., all nineteen non-cysteine amino acids or a subset thereof), a position that is varied among all possible amino acids, a position that is varied among a set of amino acids that exclude basic amino acids, or a position that allows K, R, or H.

In one embodiment, the HC CDR3 region is less than 10, 8, or 7 amino acids in length, e.g., about 5, 6, or 7 amino acids in length.

In one embodiment, the antibodies of the plurality include diverse light chain variable domains. At least some of which can be light chain variable domains other than DPL16 or and/or a light chain variable domain sequence that has a canonical structure other than that of a DPL16 light chain. The library may or may not also further include a DPL16 light chain or a variable domain sequence that has a canonical structure of a DPL16 light chain.

For example, the light chain variable domain sequence of each antibody of the plurality is encoded by nucleic acids derived from transcripts of human hematopoietic cells.

In one embodiment, the heavy chain variable domain sequences of the antibodies of the plurality have the same canonical structure. In another embodiment, the heavy chain variable domain sequences of the antibodies of the plurality include a plurality of different canonical structures. In one embodiment, the canonical structure is that of the 3-23 heavy chain VH segment.

In one embodiment, the heavy chain variable domain sequences of the antibodies of the plurality include one or more frameworks from a human germline sequence, e.g., DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54, or a framework sequence that differs by two or fewer differences (e.g., substitutions, deletions, or insertions), e.g., one difference, relative to a human germline sequence.

In one embodiment, the antibodies of the plurality include diverse HC CDR1 and/or CDR2 regions. For example, CDR1 and CDR2 of the heavy chain variable domain sequence are encoded by sequences derived from diverse synthetic oligonucleotides.

The step of identifying one or more members that interact with the target molecule can include physically separating members of the library that bind to the target molecule from members that do not bind. The target molecule can be immobilized on a insoluble support, e.g., a solid support, prior to, during, or after the step of contacting. In one embodiment, the insoluble support is an immunotube or a membrane (e.g., a nitrocellulose, nylon membrane, magnetic bead, or non-magnetic bead).

In one embodiment, the protein is a member of a phage display library. In this case, identifying one or more members that interact with the target molecule may include recovering one or more phage that encodes an antibody that binds to the target molecule.

In one embodiment, the protein library is a collection of proteins disposed on an array. In this case, step of identifying one or more members that interact with the target molecule may include imaging the array or otherwise obtaining qualitative or quantitative indications of binding interactions.

The antibodies in the library can be in a variety of forms, e.g., as a Fab, a Fab2', a domain antibody (dAb), a single chain antibody, or a full-length antibody. Not every antibody in the protein library need be fully functional. Further, the protein library may include members other than members of the plurality. In one embodiment, the members of the plurality constitute at least 10, 25, 50, 75, 80, 90, 95, 99, or 100% of the members in the protein library.

In one embodiment, the protein library is depleted of members that interact with a non-target molecule, for example, a non-sulfated version of a suflated carbohydrate.

The target molecule can be a glycosaminoglycan, e.g., a sulfated carbohydrate, e.g., heparan sulfate, dermatansulfate, Sulfated Sialyl Lewis X (sLex) moieties (for a review see, e.g., S. Hemmerich, S. Rosen (2000), *GlycoBiology* 10, 849-856) or other synthetic sulfated carbohydrate moieties. The target can be a carbohydrate having negatively charged or electronegative groups, such as carboxylic acid, sulfate, phosphate, arsonate, fluro, or nitro groups. Still other target molecules are described herein.

The method can further include evaluating interaction between (i) one or more antibodies that include CDRs from a library member identified as interacting with the target molecule and (ii) a molecule other than the target molecule. This evaluation can be used to identify antibodies that preferentially bind to the target molecule relative to another molecule, e.g., another related molecule. For example, the target molecule and the non-target molecule can include a carbohydrate moiety, e.g., different carbohydrate moieties, or the same carbohydrate moiety in different contexts (e.g., on different proteins, with a sulfate removed, or with the sulfate in a different site).

The method can further include identifying a plurality of antibodies that interact with the target molecule, and selecting a subset of antibodies from the plurality that preferentially interacts with the target molecule relative to a non-target molecule. A subset of antibodies can include one or more antibodies.

The method can further include evaluating the ability of one or more antibodies that include CDRs from a library member identified as interacting with the target molecule to modulate interaction between a cognate ligand of the target molecule and the target molecule.

The method can further include preparing a pharmaceutical composition that includes an antibody that includes CDRs from a library member identified as interacting with the target molecule. For example, the antibody in the composition includes human or effectively human framework regions and constant regions. The antibody in the composition can be humanized or deimmunized. The composition can be substantially free of sugar compounds.

An antibody coding library can be provided by modifying a pre-existing nucleic acid library or nucleic acid components, e.g., to provide a library described herein. For example, one method for providing an antibody coding library includes: providing an antibody coding library that includes a plurality of members, each member including a sequence encoding a heavy chain variable domain sequence; providing nucleic acids that encode a diverse population of HC CDR3 sequences (such as a diverse population of HC CDR3 sequences described herein), e.g., on which at least one amino acid position in CDR3 is restricted to a basic amino acid, or complements of such nucleic acids; and modifying the HC variable domain coding sequences to include the HC CDR3 coding sequence. Prior to the modifying, the HC variable domain coding sequences can be diverse among members of the plurality. The modifying can include one or more of PCR, restriction digestion and ligation.

In one embodiment, the nucleic acids that encode a diverse population of HC CDR3 sequences include oligonucleotide, e.g., synthetic oligonucleotides. Synthetic oligonucleotides can be made, for example, by chemically attaching oligonucleotide building blocks (e.g., mono- or tri-nucleotides), e.g., using phosphoramidite chemistry. In one embodiment, each oligonucleotide includes a sequence with a FR3::CDR3-coding sequence: ARG"RGT|NNK|ARG|NNK|ARG|NNK (SEQ ID NO:4), wherein positions designated by N are varied by inclusion of one of the four nucleotides (A/G/C/T) and positions designated by R are varied by inclusion one of two nucleotides (A/G) and positions designated by K are varied by inclusion one of two nucleotides (T/G), or oligonucleotides complementary to such varied oligonucleotides. In another embodiment, each oligonucleotide includes a sequence that encodes a CDR3 that includes: X-B-B-X-B-X (SEQ ID NO:1) (wherein B is a varied or invariant basic amino acid); or X-(R/K)-X-(K/R)-X (SEQ ID NO:2); or (G/S)-X-(R/K)-X-(K/R)-X (SEQ ID NO:3); or oligonucleotides complementary to such varied oligonucleotides. In addition, the nucleic acid may encode variation in framework residues adjacent to HC CDR3, for example residue 94. For example, the oligonucleotide encodes: Y-Y-C-A-(R/K)-G-X-R-X-(K/R) -X-W-G (SEQ ID NO:5) (underscored amino acids are part of FR3 or FR4) or Y-Y-C-A-(R/K)-(G/S)-X-(R/K)-X-(K/R)-X-W-G (SEQ ID NO:6).

In certain implementations, the oligonucleotide can exclude sequences that encode other CDRs, e.g., CDR1 or CDR2. The oligonucleotides can be less than 200, 150, 100, 80, or 60 nucleotides in length. The oligonucleotides can be isolated, e.g., in a preparation that is at least 10%, e.g., free of other nucleic acid species.

The method can further include expressing the members of the antibody coding library to obtain a library of proteins.

In another aspect, the disclosure features a protein library that includes a plurality of diverse antibodies, each antibody including a heavy chain variable domain sequence and a light chain variable domain sequence. In one embodiment, the heavy chain variable domain sequence of each antibody of the plurality includes diversity in HC CDR3, but at least one amino acid position is restricted to a basic amino acid.

In one embodiment, the library has a theoretical diversity of at least $10^7$, $10^9$, $10^{10}$, or $10^{11}$ different antibodies and/or fewer than $10^{18}$, $10^{16}$, $10^{14}$, $10^{12}$, $10^{11}$, or $10^{10}$ different antibodies. In one embodiment, the theoretical diversity is between $10^5$-$10^{12}$, $10^3$-$10^{15}$ or $10^8$-$10^{16}$ antibodies. The theoretical diversity refers to the total number of distinct amino acid sequences that could be encoded by the library in its completely represented form, regardless of an actual implementation. Theoretical diversity is generally the product of the number of variations at each position. For example, the theoretical diversity of varying only two positions among all twenty amino acids is 20×20, or 400. The actual library size is determined by the number of actual antibodies present in the library, e.g., the number of transformants of a display library or the number of distinct addresses on a protein array. The actual library diversity can be smaller than the theoretical diversity, e.g., between $10^5$-$10^{11}$ or between $10^3$ and $10^{15}$ antibodies, and may be larger, e.g., due to random mutations introduced during cloning.

The protein library can include one or more features described herein.

The disclosure also features an antibody coding library that includes a plurality of diverse nucleic acids, e.g., an antibody coding library described herein. Each nucleic acid can include a sequence that encodes at least a heavy chain variable domain of an antibody in a protein library described herein. The antibody coding library can include one or more features described herein.

In another aspect, this disclosure features an antibody described herein or identified by a process disclosed herein. For example, the antibody includes a HC CDR3 that includes (G/S) X-(R/K)-X-(K/R)-X (SEQ ID NO:7), wherein X is any amino acid or other motif described herein. In one embodiment, the antibody binds a molecule that includes a negatively charged carbohydrate moiety, e.g., a glycosaminoglycan, e.g., heparan sulfate or dermatan sulfate or chondroitin sulfate or a Sulfated Sialyl Lewis X moiety. For example, the antibody binds to a sulfate group in the carbohydrate, or binding is dependent on the compound being sulfated.

In one embodiment, the antibody binds to sulfated sialyl Lewis X moiety. For example, the antibody preferentially binds to a sulfated sialyl Lewis X moiety relative to a moiety that is otherwise the same, but non-sulfated (Rosen S. D. 2004, *Annu. Rev. Immunol.* 22, 129-156; Uchimura et al., 2005, *Nature Immunology* 6:1105-13; Kawashima et al, 2005, *Nature Immunology*, 6:1096-1104; Dube D. H. et al., 2005, *Nature Drug Discovery reviews* 4:477-88; Pratt et al. 2004, *Org. Lett.* 6(14):2345-48).

The antibody can include other features described herein.

In one aspect, the disclosure features an antibody that includes a heavy chain variable domain sequence and/or a light chain variable domain sequence. The antibody has an antigen binding site that interacts with the target molecule, e.g., binds with a $K_d$ of less than $10^{-7}$, $10^{-8}$, $10^{-9}$, or $10^{-10}$ molar. The antibody can bind, e.g., an epitope that includes a negatively charged moiety, e.g., a negatively charged carbohydrate moiety, e.g., a moiety described herein. The antibody can include other features described herein.

In another aspect, the disclosure features an antibody (e.g., an isolated antibody) that binds to heparan sulfate and/or chemically desulfated N-sulfated heparin (CDSNS) and has (a) a HC immunoglobulin variable domain sequence comprising one or more CDRs that are at least 85, 88, 90, 92, 94, 95, 96, 97, 98, 99, or 100% identical to a CDR of a HC variable domain described herein; (b) a LC immunoglobulin variable domain sequence comprising one or more CDRs that are at least 85, 88, 90, 92, 94, 95, 96, 97, 98, 99, or 100% identical to a CDR of a LC variable domain described herein; (c) a LC immunoglobulin variable domain sequence is at least 85, 88, 90, 92, 94, 95, 96, 97, 98, 99, or 100% identical to a LC variable domain described herein; or (d) a HC immunoglobulin variable domain sequence is at least 85, 88, 90, 92, 94, 95, 96, 97, 98, 99, or 100% identical to a HC variable domain described herein. In some embodiments, such antibodies will have a HC CDR3 domain that is at least 85, 88, 90, 92, 94, 95, 96, 97, 98, 99, or 100% identical to a CDR3 of a HC variable domain of a HS-binding antibody described herein.

In a further aspect, the disclosure features an antibody (e.g., an isolated antibody) that binds to sulfocore 6 and has (a) a HC immunoglobulin variable domain sequence comprising one or more CDRs that are at least 85, 88, 90, 92, 94, 95, 96, 97, 98, 99, or 100% identical to a CDR of a HC variable domain described herein; (b) a LC immunoglobulin variable domain sequence comprising one or more CDRs that are at least 85, 88, 90, 92, 94, 95, 96, 97, 98, 99, or 100% identical to a CDR of a LC variable domain described herein; (c) a LC immunoglobulin variable domain sequence is at least 85, 88, 90, 92, 94, 95, 96, 97, 98, 99, or 100% identical to a LC variable domain described herein; or (d) a HC immunoglobulin variable domain sequence is at least 85, 88, 90, 92, 94, 95, 96, 97, 98, 99, or 100% identical to a HC variable domain described herein. In some embodiments, such antibodies will have a HC CDR3 domain that is at least 85, 88, 90, 92, 94, 95, 96, 97, 98, 99, or 100% identical to a CDR3 of a HC variable domain of a SC6-binding antibody described herein.

In another aspect, this disclosure features a pool of oligonucleotides that includes a plurality of different oligonucleotides. Each oligonucleotide of the plurality includes a sequence with a CDR3-coding sequence. In one embodiment, the CDR3 coding sequence encodes (G/S)-X-(R/K)-X-(K/R)-X (SEQ ID NO:7), wherein X can be any amino acid, and (K/R) can be either lysine or arginine and G and S can either be a serine or glycine. In another embodiment, the DNA sequence includes RGT|NNK|ARG|NNK|ARG|NNK (SEQ ID NO:8), wherein positions designated by N are varied by inclusion of one of the four nucleotides (A|G/C|T) and positions designated by R are varied by inclusion one of two nucleotides (A/G) and positions designated by K are varied by inclusion one of two nucleotides (T/G), or oligonucleotides complementary to such varied nucleotides. The CDR3 coding sequence can be flanked by one or more of a sequence encoding at least a portion of FR3 and a sequence encoding at least a portion of FR4.

In another aspect, the disclosure features a method for identifying an antibody that binds to a polypeptide with a negatively charged modification, e.g., a phosphorylated polypeptide or phosphocarbohydrate. The method includes: providing a protein library that includes a plurality of diverse antibodies, each antibody including a heavy chain variable domain sequence and/or a light chain variable domain sequence, contacting members of the protein library to a target molecule that includes a negatively charged modification; and identifying one or more members that interact with the target molecule.

The method can be used to identify an antibody to target molecule having a negatively charged modification, e.g., by binding to an epitope that includes the negatively charged modification, and may further include confirming that the antibody interacts with (e.g., binds to) the target molecule and/or epitope. For example, the method is used to identify an antibody to a phosphorylated intracellular polypeptide.

In one embodiment, the heavy chain variable domain sequence includes diversity in HC CDR3, but at least one or two amino acid positions are restricted to a basic amino acid. Restricted positions can be, independently, completely invariant, or can be allowed to vary among basic amino acids. For example, one basic amino acid position is an invariant arginine, and another basic amino acid position is allowed to vary between arginine and lysine. At least two of the basic amino acid positions can be separated by at least one amino acid position that is allowed to vary among at least ten different amino acids. For example, for each antibody of the plurality, HC CDR3 includes X-B-B-X-B-X (SEQ ID NO:1) (wherein B is a varied or invariant basic amino acid); or X-(R/K)-X-(K/R)-X (SEQ ID NO:2); or (G/S)-X-(K/R)-X-(K/R)-X (SEQ ID NO:3). In one embodiment, X is any amino acid. In another embodiment, X represents positions that are varied among at least four, six, ten, twelve, or sixteen different amino acids. For example, X can represent, independently, a position that is varied among non-cysteine amino acids (e.g., all nineteen non-cysteine amino acids or a subset thereof), a position that is varied among all possible amino acids, or a position that is varied among a set of amino acids that exclude basic amino acids.

In one embodiment, the HC CDR3 region is less than 10, 8, or 7 amino acids in length, e.g., about 6 or 7 amino acids in length.

The method can include other features described herein.

In another aspect, the disclosure features a method for evaluating an antibody. The method includes providing an antibody that includes a HC CDR3 that includes an amino acid sequence that conforms to a motif described herein or that includes two or more basic amino acids or that has a property otherwise described herein; and contacting the antibody to a target molecule, e.g., a polypeptide that includes a carbohydrate moiety or a polypeptide with a negatively charged modification, e.g., a phosphorylated polypeptide; and evaluating a parameter associated with binding.

In one embodiment, the HC CDR3 includes at least one basic amino acid position, e.g., arginine or lysine. For example, the HC CDR3 includes at least two of the basic amino acid positions, e.g., positions separated by at least one non-basic amino acid position s. For example, HC CDR3 includes X-B-B-X-B-X (SEQ ID NO:1) (wherein B is a varied or invariant basic amino acid); or X-(R/K)-X-(K/R)-X (SEQ ID NO:2); or (G/S)-X-(K/R)-X-(K/R)-X (SEQ ID NO:3). In one embodiment, X is any amino acid, e.g., a non-basic amino acid. In one embodiment, the HC CDR3 region is less than 10, 8, or 7 amino acids in length, e.g., about 6 or 7 amino acids in length.

Other features and advantages will become more apparent from the following detailed description and claims. Embodiments can include any combination of features described herein. The contents of all references, pending patent applications and published patents, cited throughout this application are hereby expressly incorporated by reference.

BRIEF DESCRIPTION OF THE DRAWINGS

FIG. 3A-3H shows the annotated Fab display cassette incorporated in the FAB-310 library. SEQ ID NO:25 is a portion of the cassette encoding nucleotide sequence of light chain variable region (VL). SEQ ID NO:26 is a portion of the cassette encoding amino acid sequence of light chain variable region (VL). SEQ ID NO:27 is a portion of the cassette encoding nucleotide sequence of light chain constant region (CL). SEQ ID NO:28 is a portion of the cassette encoding amino acid sequence of light chain constant region (CL). SEQ ID NO:29 is a portion of the cassette encoding nucleotide sequence of heavy chain variable region (VH). SEQ ID NO:30 is a portion of the cassette encoding amino acid sequence of heavy chain variable region (VH). SEQ ID NO:31 is a portion of the cassette encoding nucleotide sequence of heavy chain 1 constant region (CH1). SEQ ID NO: 32 is a portion of the cassette encoding amino acid sequence of heavy chain 1 constant region (CH1).

DETAILED DESCRIPTION

Figure 1:
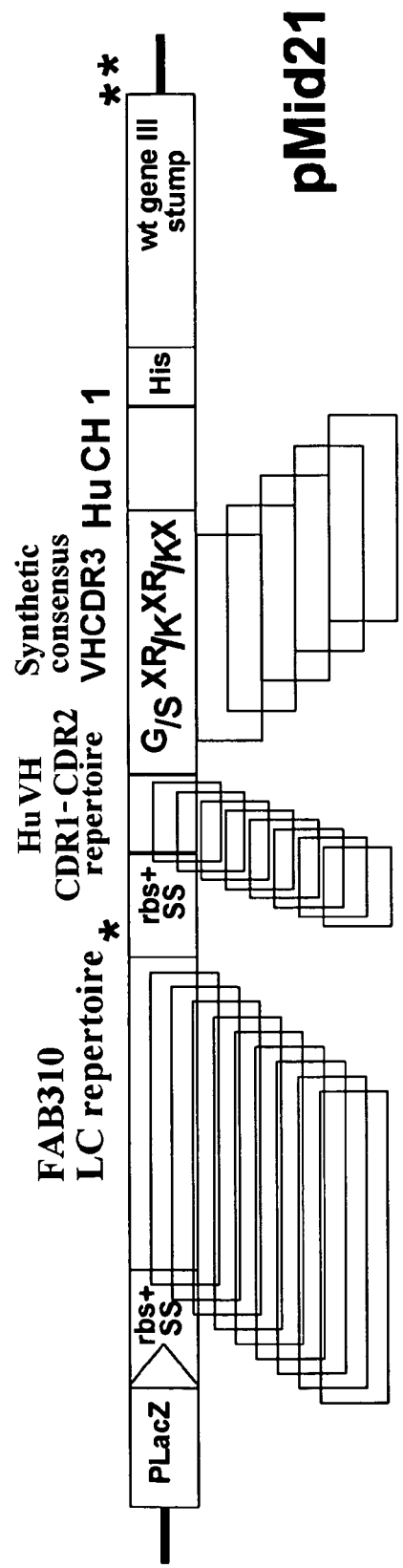
FIG. 1 is a schematic of the Library of Example 1. The Fab display cassette having captured kappa and lambda LC and synthetic diversity in HC CDR1 and CDR2 as described in Hoet et al. (*Nature Biotechnology*, 2005, 23(3):344-8. HC CDR3 is as described in Example 1.

We have discovered, inter alia, that certain structural properties are beneficial for immunoglobulins that interact with carbohydrates. While some antibodies specific for carbohydratese have been reported in the scientific literature (see, e.g., Dennissen et al. JBC (2002) 277(13):10982-86; Bernsen et al. *Cancer Immunol Immunother*. (2003) 52(12):780-83; Dinh et al. *J. Immunol*. 1996 157(2):732-38; Mao et al. *Proc. Nat'l Acad. Sci USA* (1999) 96(12):6953-58; Streeter et al., (1988) *J. Cell. Biol*. 107(5):1853-62; Reason et al. *Infect Immun*. (1997) 65(1)261-6; van Kuppevelt et al. *J. Biol. Chem*. (1998) 273:12960-66; Jenniskens et al. *J. NeuroSci*. (2000) 20(11):4099-111; Chen et al. *Mol. Immunol*.(2000) 37(8):455-66; van de Westerlo et al. *Blood* (2002) 99(7): 2427-33; Willats et al. *Plant J*. (1999) 18(1):57-65; Chang & Siegel *Transfusion* (2001) 41(1):6-1; Lee et al. *J. Am. Chem. Soc*. (2002) 124:12439-46; Kowal et al. *Eur. J. Immunol*. (1999) 29(6):1901-11; Nguyen et al, *Nat. Struct. Biol*. (2003) 10(12):1019-25; Wang et al. *Mol. Immunol*. (1997) 34(8-9): 609-18; Haidaris et al. *J. Immunol. Meth*. 2001 257(1-2):185-202; Foy et al. *J. Immunol. Meth*. (2002) 261(1-2):73-83), such antibodies are considered difficult to obtain. Libraries that include a significant number of immunoglobulins with the properties disclosed herein can be used as a source of immunoglobulins that interact with carbohydrates, especially negatively charged carbohydrates.

In one implementation, we produced a phage display library that displays antibodies in a Fab format. The library was used to identify antibodies that bind to an epitope that includes a carbohydrate moiety.

A general strategy for providing an enriched library includes identifying proteins that specifically interact with a target of interest, e.g., a target with reduced immunogenicity or an epitope of interest, e.g., an epitope with reduced immunogenicity, identifying a consensus sequence present in the proteins (e.g., some or all of the proteins), and preparing a protein library in which at least 10%, 50%, 80% or all the members include a sequence that conforms to the identified consensus. Targets with reduced immunogenicity include those with highly charged properties and those that have features that are prevalent among self-antigens. In one implementation, the method is used for immunoglobulin proteins, although it is applicable to any type of protein, particularly proteins with a conserved scaffold domain. The library need not be a phage display library but can be another form of expression library, a protein array, a two-hybrid library, and so forth.

A number of properties are useful in antibodies that bind to carbohydrates, particularly negatively charged carbohydrates. Exemplary antibodies may have one or more of the following properties:

a small HC CDR3 sequence, e.g., less than 12, 11, or 10 amino acids, e.g., about 7-8 amino acids;

at least one or two basic residues, e.g., two arginines, in one or more CDRs, e.g., HC CDR3;

a motif, such as XBBXBX (SEQ ID NO:1) (where B, basic amino acid residue; X, any amino acid residue or any non-cysteine amino acid) in HC CDR3; and a motif such as (G/S)-X-(R/K)-X-(R/K)-X (SEQ ID NO:9) (where X, any amino acid residue or any non-cysteine amino acid) in HC CDR3;

variation of FR3 at the last residue between R and K.

An antibody library can include a plurality of proteins with one or more of these properties.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$, a Fd fragment, a Fv fragments, and dAb fragments) as well as complete antibodies. Antibodies with only a single variable domain have also been described, e.g., a soluble VH domain or a camelid V domain. Davies et al. (1996) *Immunotechnology* 2:169-179, for example, describes synthetic VH domains that bind to antigen in the absence of a VL domain.

The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest*, Fifth Edition, U.S. Department of Health and Human Services, NIH Publication No. 91-3242, and Chothia, C. et al. (1987) *J. Mol. Biol*. 196:901-917).

Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

The canonical structures of hypervariable loops of an immunoglobulin variable are structural properties. Typically, the canonical structure of a particular loop can be inferred from its sequence, as described in Chothia et al. (1992) *J. Mol. Biol.* 227:799-817; Tomlinson et al. (1992) *J. Mol. Biol.* 227: 776-798); and Tomlinson et al. (1995) *EMBO J.* 14(18):4628-38. Further, the CDR sequences of a particular germline antibody can provide amino acid residues for a hypervariable loop that result in a particular canonical structure.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405). Although highly conserved, the disulfide is not absolutely required. An "immunoglobulin variable domain sequence" refers to an amino acid sequence that can form a structure that enables the CDR regions and/or hypervariable loops to form an antigen binding structure. The sequence may include at least two or all three CDRs and sufficient framework amino acids to position the CDRs. The sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site").

The comparison of sequences and determination of percent identity between two sequences can be performed using BLAST (Altschul et al. (1990) *J. Mol. Biol.* 215:403-410), particularly BLAST 2 Sequences as described by Tatusova and Madden (1999, *FEMS Microbiol. Lett.* 174:247-250) and as implemented by the National Center for Biotechnology Information (available via the world wide web at ncbi.nlm.nih.gov/blast/bl2seq/wblast2.cgi). Parameters for comparison of two nucleotide sequences (e.g., BLASTN) are Reward for a match: 1; Penalty for a mismatch:−2; Open gap penalty: 5; extension penalty gap: 2; gap x_dropoff: 50; expect: 10.0; word size: 11. Parameters for comparison of two amino acid sequences (e.g., BLASTP) are Matrix: BLOSUM62; Open gap penalty: 11; extension gap penalty: 1; gap x_dropoff: 50; expect: 10.0; and word size 3.

Carbohydrate Targets

Exemplary carbohydrate molecules that can serve as target molecules include glycosaminoglycans, negatively charged glycoproteins, and, generally, any molecule that includes at least one negatively charged saccharide moiety. Saccharides can have negative charge or high negative partial charges due to the presence of groups such as (without limitation) carboxylic acid, sulfate, phosphate, arsonate, nitrate, flouride, or chloride groups.

Some examples of carbohydrate molecules include heparin and heparan sulfates. Heparan sulfate (HS) refers to one heterogeneous class of glycosaminoglycans. exemplary forms of heparan sulfates include dermatan sulfate, chondroitin 4- and 6-sulfate, keratan sulfate. Examples of synthetic heparan sulfate oligosaccharide moieties include: GlcNac6S-GlcUAαMe, IdoUA-GlcNAc-GlcUA Me; GlcNS6S-GlcUA-GlcNS6S Me; GlcN-GlcUA-GlcN Me; IdoUA2S-GlcNS6S-IdoUA2S-GlcNS6S Me; GlcUA-GlcNS-GlcUA-GlcNS-IdoUA2S Me; IdoUA-GlcNS-GlcUA-GlcNS-IdoUA2S Me;GlcUA-GlcNS-IdoUA-GlcNS-IdoUA2S Me; GlcNS6S-GlcUA-GlcNS36diS-IdoUA2S-GlcNS36diS Me; GlcNS6S-GlcUA-GlcNS36diS-IdoUA2S-GlcNS6S Me; GlcNS6S-GlcUA-GlcNS36diS-IdoUA-GlcNS Me; and GlcNS6S-GlcUA-GlcNS36diS-IdoUA-GlcNS6S Me.

Other exemplary carbohydrate targets include dextran sulfate, hyaluronate, and K5 polysaccharide from *E. coli*. In some embodiments, the target molecule is a complex, e.g., of a protein and a carbohydrate molecule, e.g., heparin bound by anti-thrombin III, or heparan sulfate and basic fibroblast growth factor (bFGF).

Heparan sulfates can be synthesized in vitro or obtained from a tissue source, e.g., kidney, aorta, lung, or intestine, e.g., from an animal, e.g., a human source or other mammal.

To evaluate whether an antibody recognizes a structure that depends on a sulfate group, the target molecule can be modified, e.g., chemically. It is possible to strip target molecules of their O- and N-sulfate groups. For example, $HNO_2$ at pH 1.5 can be used to cleave at N-sulfated glucosamine residues (GlcNs) and at rare N-unsubstituted glucosamine residues. See, e.g., van Kuppevelt (1998) *J. Biol. Chem.* 273:12960-12966.

Also, one can modify the target molecule using enzymes, e.g., a heparinase (e.g., heparinase III), a chondrointinase (e.g., chondroitinase ABC). An antibody that only interacts with the target molecule prior to modification is likely to specifically recognize a structure affected by the modification.

Further using appropriate binding and/or functional assays, it is possible to obtain antibodies that modulate biological interactions, e.g., an interaction between a carbohydrate molecule and a cognate protein ligand that recognizes a moiety on the carbohydrate molecule. For example, antibodies can be identified that modulate (e.g., increase or decrease) the binding interaction between heparin and anti-thrombin III or between heparan sulfate and bFGF. HS is involved in the binding of growth factors such as neuregulin (see, e.g., Fischbach and Rosen, *Ann Rev Neurosci* 20 (429-458)) midkine (see, e.g., Zhou et al., (1997) *Neurosci* 10:56-70), and heparin-binding epidermal factor-like growth factor (see, e.g., Chen et al. 1995, *J. Biol. Chem.*, 270:18285-94)

HS is also involved in molecules involved in leucocyte adhesion and function has been implicated in tumor cell invasion and angiogenesis (e.g., Vlodavsky I. et al. (1990) *Cancer Metastasis Rev.* 9 203, Iozzo R. V. et al. (2001), *J. Clin. Invest.* 108: 349-355. The different functional features of HS seem to be linked to the amount and location of its sulfate groups (e.g., Salmivirta M. et al. (1996), *FASEB J.* 10: 1270). Accordingly, an antibody described herein can be used to treat or prevent a neoplastic disorder, particularly one that is associated with angiogenesis or tumor cell invasion.

Other examples of biological relevant interactions include those mediated by endothelial ligands for L-Selectin (sulfated carbohydrate moieties), for example present on GlyCAM-1, CD34, Sgp200, Podocalyxin. See, e.g., Rosen, 1999, *Am J. Pathology,* 155:1013-20; Rosen, 2004, *Annu. Rev. Immunol.* 22:129-56; Dube et al., 2005, *Nature Drug Discovery reviews*, 4:477-488; Pratt et al., 2004, *Org Lett.* 6(14):2345-48.

Antibodies that decrease a binding interaction can, for example, block a binding site on the carbohydrate molecule recognized by the cognate protein ligand. Antibodies that increase a binding interaction can, for example, stabilize an interaction between the carbohydrate molecule and the cognate protein ligand.

Other useful targets include ones in which the target is associated with, produced by, or presented by a pathogen, e.g., a bacterial pathogen, e.g., as mentioned herein.

Still another class of targets includes targets that are present on tumor cells or tumor-associated structures. For example, the target is an antigen present on a tumor cell in at least 2, 5, or 10 fold greater abundance than on a normal cell, an antigen the glycolipid class, including acidic glycolipid such as, for example, gangliosides GD2, GD3 and GM3 (melanoma) and neutral glycolipids such as, for example, the Lewis$^y$ (Le$^y$) (breast, prostate, ovary) and the Globo H (breast, prostate, ovary) antigens, and/or sialylated derivatives thereof; O-glycosyl peptides (or aminoacid) class such as, for example, the Tn antigen (αGalNAc-Ser or αGal NAc-Thr), T* antigen (βGal-(1-3)-α-GalNac-Ser or βGal(1-3) αCalNAc-Thr) (see, e.g., Springer G. F. Science 224, 1198-1206 (1984)) (ovary, breast, lung), or di-Tri (α GalNAc-Ser/Thr)$_2$, tri-Tn(α GalNac-Ser/Thr)$_3$ or hexa-Tn(αGalNAc-Ser/Thr)$_6$.

Phospho-Polypeptide Targets

Another class of targets include proteins that have a phosphate group, e.g., as a result of phosphorylation. Exemplary proteins contain one or multiple negatively charged phosphate groups, for example Phospho-Tyrosine or Phospho-Serine. Examples of phosphorylated proteins include kinases, transcription factors, tyrosine kinase receptors, and adaptor proteins. Antibodies to such proteins can be used for a variety of purposes, including detecting the presence of the phosphorylated form of such proteins.

Antibody Libraries

An antibody library is a collection of proteins that include proteins that have at least one immunoglobulin variable domain sequence. For example, camelized variable domains (e.g., VH domains) can be used as a scaffold for a library of proteins that include only one immunoglobulin variable domain sequence. In another example, the proteins include two variable domains sequences, e.g., a VH and VL domain, that are able to pair. An antibody library can be prepared from a nucleic acid library (an antibody-coding library) that includes antibody-coding sequences.

In cases where a display library is used, each member of the antibody-coding library can be associated with the antibody that it encodes. In the case of phage display the antibody protein is physically associated (directly or indirectly) with a phage coat protein. A typical antibody display library displays a polypeptide that includes a VH domain and a VL domain. The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are included. It is also possible to add one or more constant regions to a molecule after it is identified as having useful antigen binding site. See, e.g., US 2003-0224408.

Antibody libraries can be constructed by a number of processes (see, e.g., de Haard et al. (1999) *J. Biol. Chem* 274: 18218-30; Hoogenboom et al. (1998) *Immunotechnology* 4:1-20, Hoogenboom et al. (2000) *Immunol Today* 21:371-8, and Hoet et al. (2005) *Nat Biotechnol.* 23(3):344-8. Further, elements of any appropriate known process can be combined with those of other processes. Variation can be introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into HC CDR3. In one embodiment, variation is introduced into all three CDRs of a given variable domain. In another preferred embodiment, the variation is introduced into CDR1 and CDR2, e.g., of a heavy chain variable domain. Any combination is feasible.

Antibody-coding libraries can be constructed by a variety of methods. In one exemplary process, antibody-coding libraries are constructed by inserting diverse oligonucleotides that encode CDRs into the corresponding regions of an antibody-coding nucleic acid. A population of diverse oligonucleotides can be synthesized using pools of different monomeric nucleotides or pools of different trinucleotides. The inclusion of a given element (e.g., a given nucleotide) is random with respect to the distribution and may only depend on the ratio of subunits in the pool. One example of a degenerate source of synthetic diversity is an oligonucleotide that includes NNN wherein N is any of the four nucleotides in equal proportion or some other desired proportion.

Synthetic diversity can also be more constrained, e.g., to limit the number of codons in a nucleic acid sequence at a given trinucleotide to a distribution that is smaller than NNN. For example, such a distribution can be constructed using less than four nucleotides at some positions of the codon. Mixtures of mononucleotides can be used to vary a codon, e.g., between two, three, four, eight, or other numbers of amino acid types.

In addition, trinucleotide addition technology can be used to obtain more particularized distributions. So-called "trinucleotide addition technology" is described, e.g., in Wells et al. (1985) *Gene* 34:315-323, Knappik et al. (2000) *J. Mol. Biol.* 296:57-86; U.S. Pat. Nos. 4,760,025 and 5,869,644. Oligonucleotides are synthesized on a solid phase support, one codon (i.e., trinucleotide) at a time. The support includes many functional groups for synthesis such that many oligonucleotides are synthesized in parallel. The support is first exposed to a solution containing a mixture of the set of codons for the first position. The unit is protected so additional units are not added. The solution containing the first mixture is washed away and the solid support is deprotected so a second mixture containing a set of codons for a second position can be added to the attached first unit. The process is iterated to sequentially assemble multiple codons. Trinucleotide addition technology enables the synthesis of a nucleic acid that at a given position can encode a number of amino acids. The frequency of these amino acids can be regulated by the proportion of codons in the mixture. Further the choice of amino acids at the given position is not restricted to blocks of the codon table as is the case if mixtures of single nucleotides are added during the synthesis.

These and other methods can be used prepare oligonucleotides that include one or more codons that are constrained to a basic amino acid (e.g., arginine or lysine), to potentially positively charged amino acids (e.g., histidine, arginine, or lysine), or to vary among such combinations of codons. The oligonucleotide can include other positions that are more varied, e.g., varied among all possible amino acids, non-cysteine amino acids, aliphatic amino acids, hydrophilic amino acids, and so on. The oligonucleotide can include a pattern of variation described herein.

The oligonucleotides in a population of diverse oligonucleotide can also include positions at which all the oligonucleotides have the same nucleotide. For example, the termini typically include at least 5, 10, 15, 18, or 20 nucleotides that are invariant.

Components of antibody coding libraries can be obtained from nucleic acid amplified from naïve germline immunoglobulin genes or from mRNA expressed by antibody producing cells. The amplified nucleic acid includes nucleic acid encoding the VH and/or VL domain or a region thereof, e.g., a framework or constant region. Sources of immunoglobulin-encoding nucleic acids are described below. Amplification can include PCR, e.g., with one or more primers that anneal to one or more conserved regions, or another amplification method. Nucleic acid encoding immunoglobulin domains can be obtained from the immune cells of, e.g., a human, a primate, mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In still another embodiment, the cells are isolated from a subject that has an immunological disorder, e.g., systemic lupus erythematosus (SLE), rheumatoid arthritis, vasculitis, Sjogren syndrome, systemic sclerosis, or anti-phospholipid syndrome. The subject can be a human, or an animal, e.g., an animal model for the human disease, or an animal having an analogous disorder. In yet another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al. (2001) *J Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs. The reverse transcription of the first (antisense) strand can be done in any manner with any suitable primer. See, e.g., de Haard et al. (1999) *J. Biol. Chem* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes). A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity. The variable domain-encoding gene is then amplified, e.g., using one or more rounds. If multiple rounds are used, nested primers can be used for increased fidelity. The amplified nucleic acid is then cloned into a display library vector.

Antibody libraries are particularly useful, for example for identifying human or "humanized" antibodies that recognize human antigens. Such antibodies can be used as therapeutics to treat human disorders. Antigen binding sites identified from antibody libraries can be modified, for example, fused to human constant regions or modified human constant regions. Since the constant and framework regions of the antibody are human, these therapeutic antibodies may avoid themselves being recognized and targeted as antigens. The constant regions may also be optimized to recruit effector functions of the human immune system. The in vitro display selection process surmounts the inability of a normal human immune system to generate antibodies against self-antigens. Other types of antibody expression libraries can be used, including, e.g., protein arrays of antibodies (see, e.g., De Wildt et al. (2000) *Nat. Biotechnol.* 18:989-994), lambda gt11 libraries, and so forth.

One exemplary antibody library is described in US 2002102613. A pre-existing antibody coding library can be modified, e.g., to replace CDR3-coding sequences with oligonucleotides designed to encode CDR3 sequences that are biased for carbohydrate binding. For example, the oligonucleotides can encode CDR3 sequences of a particular length, e.g., less than ten, nine, or eight amino acids in length, e.g., about seven or six amino acids in length. The oligonucleotides can include one or positions that are preferentially basic (e.g., have at least a 20% likelihood of being basic) or which are invariant (e.g., always arginine, always lysine, or allowed to vary between arginine and lysine).

Antibodies isolated from the libraries of the present disclosure are analyzed to determine the type of the LC and the closest germline gene. In a preferred embodiment, non-germline framework residues are changed back to the germline amino acid so long as binding affinity and specificity are not adversely affected to an unacceptable extent. The substitutions may be done as a group or singly.

Display Libraries

In one embodiment, a display library can be used to screen a collection of proteins that includes proteins biased for a particular property, e.g., ability to bind to carbohydrates, particularly negatively charged carbohydrates.

A display library is a collection of entities; each entity includes an accessible protein component and a recoverable component that encodes or identifies the protein component. The protein component can be of any length, e.g. from one amino acids to over 400 amino acids. In a selection, the protein component is probed with a target molecule and if the protein component binds to the target molecule, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the protein component and purification of the protein component for detailed characterization. A variety of formats can be used for display libraries. Examples include the following.

Phage Display. One format of display utilizes viruses, particularly bacteriophages. This format is termed "phage display." The protein component is typically covalently linked to a bacteriophage coat protein. The linkage results form translation of a nucleic acid encoding the protein component fused to a gene fragment encoding a functional portion of a coat protein of the phage. The linkage can include a flexible peptide linker, a protease site, or an amino acid incorporated as a result of suppression of a stop codon. Phage display is described, for example, in Ladner et al., U.S. Pat. No. 5,223, 409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clackson et al. (1991) *Nature* 352: 624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; Barbas et al. (1991) *PNAS* 88:7978-7982; Hoet et al. (2005) *Nat Biotechnol.* 23(3):344-8.

The filamentous phage display systems typically use fusions to a minor coat protein, such as gene III protein or a domain of the gene III protein, e.g., the anchor domain or "stump" (see, e.g., U.S. Pat. No. 5,658,727 for a description of the gene III protein anchor domain). It is also possible to physically associate the protein being displayed to the coat using a non-peptide linkage, e.g., a non-covalent bond or a non-peptide covalent bond. For example, a disulfide bond and/or heterodimerization domains can be used for physical associations (see, e.g., Crameri et al. (1993) *Gene* 137:69 and WO 01/05950). Phage display can use virus with a complete phage genome, but also phagemids which are prepared with helper phage.

Other types of protein display include cell-based display (see, e.g., WO 03/029,456.); ribosome display (see, e.g., Mattheakis et al. (1994) *Proc. Natl. Acad. Sci. USA* 91:9022 and Hanes et al. (2000) *Nat Biotechnol.* 18:1287-92); protein-nucleic acid fusions (see, e.g., U.S. Pat. No. 6,207,446); and immobilization to a non-biological tag (see, e.g., U.S. Pat. No. 5,874,214).

Iterative Selection. In one preferred embodiment, display library technology is used in an iterative mode. A first display library is used to identify one or more ligands for a target. These identified ligands are then varied using a mutagenesis method to form a second display library. Higher affinity ligands are then selected from the second library, e.g., by using higher stringency or more competitive binding and washing conditions.

In some implementations, the mutagenesis is targeted to regions known or likely to be at the binding interface. If, for example, the identified ligands are antibodies, then mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements. Likewise, if the identified ligands are enzymes, mutagenesis can be directed to the active site and vicinity.

Some exemplary mutagenesis techniques include: error-prone PCR (Leung et al. (1989) *Technique* 1:11-15), recombination, DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zoller et al. (1987) *Nucl Acids Res* 10:6487-6504), cassette mutagenesis (Reidhaar-Olson (1991) *Methods Enzymol.* 208:564-586) and incorporation of degenerate oligonucleotides (Griffiths et al. (1994) *EMBO J.* 13:3245).

In one example of iterative selection, the methods described herein are used to first identify a antibody from a display library that binds a target molecule with at least a minimal binding specificity for a target or a minimal activity, e.g., an equilibrium dissociation constant for binding of less than 100 nM, 50 nM, 10 nM, 5 nM, or 1 nM. The nucleic acid sequences encoding the initially identified antibodies are used as template nucleic acids for the introduction of variations, e.g., to identify a second antibody that has enhanced properties (e.g., binding affinity, kinetics, or stability) relative to the initial antibody.

One preferred embodiment involves diversification of an antibody selected from a library of the present disclosure having a desired specificity but either insufficient affinity or less than perfect specificity. One preferred embodiment involves preparing a secondary library in which HC is held constant and a diversity of LC is provided, e.g. the diversity of FAB-310. One preferred embodiment involves preparing a secondary library in which HC CDR3 and LC are held constant and a diversity of HC CDR1 & CDR2 is provided, e.g. the CDR1 & 2 diversity of FAB-310. One preferred embodiment involves preparing a secondary library in which HC CDR1 & CDR2 and LC are held constant and a diversity of HC CDR3 is provided, e.g. a diversity based on the selected CDR3.

Off-Rate Selection. Since a slow dissociation rate can be predictive of high affinity, particularly with respect to interactions between polypeptides and their targets, the methods described herein can be used to isolate ligands with a desired kinetic dissociation rate (i.e. reduced) for a binding interaction to a target.

To select for slow dissociating antibodies from a display library, the library is contacted to an immobilized target. The immobilized target is then washed with a first solution that removes non-specifically or weakly bound antibodies. Then the bound antibodies are eluted with a second solution that includes a saturating amount of free target, i.e., replicates of the target that are not attached to the particle. The free target binds to antibodies that dissociate from the target. Rebinding of the eluted antibodies is effectively prevented by the saturating amount of free target relative to the much lower concentration of immobilized target.

The second solution can have solution conditions that are substantially physiological or that are stringent (e.g. low pH, high pH, or high salt). Typically, the solution conditions of the second solution are identical to the solution conditions of the first solution. Fractions of the second solution are collected in temporal order to distinguish early from late fractions. Later fractions include antibodies that dissociate at a slower rate from the target than biomolecules in the early fractions. Further, it is also possible to recover antibodies that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards antibodies that bind to a non-target molecule. Examples of non-target molecules include, e.g., a carbohydrate molecule that differs structurally from the target molecule, e.g., a carbohydrate molecule that has a different biological property from the target molecule. In the case of a sulfated carbohydrate, a non-target may be the same carbohydrate without the sulfate or with the sulfate in a different position. In the case of a phosphopeptide, the non-target may be the same peptide without the phosphate or a different phosphopeptide.

In one implementation, a so-called "negative selection" step is used to discriminate between the target and related non-target molecule and a related, but distinct non-target molecules. The display library or a pool thereof is contacted to the non-target molecule. Members that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to the target.

Other Expression Libraries

Other types of collections of antibodies (e.g., expression libraries) can be used to identify antibodies with a particular property. Such other examples include, e.g., protein arrays of antibodies (see, e.g., De Wildt et al. (2000) *Nat. Biotechnol.* 18:989-994), lambda gt11 libraries, two-hybrid libraries and so forth.

Assays

Methods for evaluating antibodies for carbohydrate binding include ELISA, immunohistochemistry, immunoblotting, and fluorescence-activated cell sorting.

These methods can be used to identify antibodies which have a $K_D$ of better than a threshold, e.g., better than 0.1 µM, 50 nM, 10 nM, 5 nM, 1 nM, or 0.5 nM.

ELISA. Proteins encoded by a display library can also be screened for a binding property using an ELISA assay. For example, each protein is contacted to a microtitre plate whose bottom surface has been coated with the target, e.g., a limiting amount of the target. The plate is washed with buffer to remove non-specifically bound polypeptides. Then the amount of the protein bound to the plate is determined by probing the plate with an antibody that can recognize the polypeptide, e.g., a tag or constant portion of the polypeptide. The antibody is linked to an enzyme such as alkaline phosphatase, which produces a calorimetric product when appropriate substrates are provided. The protein can be purified from cells or assayed in a display library format, e.g., as a fusion to a filamentous bacteriophage coat. Alternatively, cells (e.g., live or fixed) that express the target molecule, e.g., a target that contains a carbohydrate moiety, can be plated in a microtitre plate and used to test the affinity of the peptides/antibodies present in the display library or obtained by selection from the display library.

In another version of the ELISA assay, each polypeptide of a diversity strand library is used to coat a different well of a microtitre plate. The ELISA then proceeds using a constant target molecule to query each well.

Cell Binding Assays. Antibodies can be evaluated for their ability to interact with one or more cell types, e.g., a hematopoietic cell. Fluorescent activated cell sorting (FACS) is one exemplary method for testing an interaction between a protein and a cell. The antibody is labeled directly or indirectly with a fluorophore, before or after, binding to the cells, and then cells are counted in a FACS sorter.

Other cell types can be prepared for FACS by methods known in the art.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate polypeptide is attached to the display library vehicle, e.g., a bacteriophage.

Surface Plasmon Resonance (SPR). The binding interaction of a molecule isolated from a display library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Protein Arrays. Proteins identified from the display library can be immobilized on a solid support, for example, on a bead or an array. For a protein array, each of the polypeptides is immobilized at a unique address on a support. Typically, the address is a two-dimensional address. Methods of producing polypeptide arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289: 1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

Pharmaceutical Compositions

An antibody identified by a method described herein can be formulated as a composition, e.g., a pharmaceutically acceptable composition, for example with a pharmaceutically acceptable carrier. The carrier can be suitable for intravenous, intramuscular, subcutaneous, parenteral, spinal or epidermal administration (e.g., by injection or infusion) to a subject, e.g., a human subject. The composition can be administered in an amount and for a time effective to ameliorate a condition, e.g., a condition described herein.

Compositions that include a protein described herein may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for administration of humans with antibodies. The preferred mode of administration is parenteral (e.g., intravenous, subcutaneous, intraperitoneal, intramuscular).

The composition can be formulated as a solution, microemulsion, dispersion, liposome, or other ordered structure suitable to high drug concentration. Sterile injectable solutions can be prepared by incorporating the active compound (i.e., the ligand) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies can be administered by a variety of methods known in the art. For many applications, the route of administration is intravenous injection or infusion. The route and/or mode of administration can vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Pharmaceutical compositions can be administered with medical devices known in the art, e.g., an implantable pump, a needleless hypodermic injection device, or a stent.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody is 0.1-20 mg/kg, more preferably 1-10 mg/kg. An antibody can be administered by intravenous infusion at a rate of less than 30, 20, 10, 5, or 1 mg/min to reach a dose of about 1 to 100 mg/m$^2$ or about 5 to 30 mg/m$^2$. It is to be noted that dosage values may vary with the type and severity of the condition to be alleviated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the disclosure may include a "therapeutically effective amount" or a "prophylactically effective amount" of an antibody. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein ligand to elicit a desired response in the individual. A therapeutically effective amount is also one in which any toxic or detrimental effects of the composition is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. Even more preferably, the "therapeutically effective dose" causes tumor stasis or regression. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

An antibody described herein can be used in a method of targetting a cell, tissue, or biological structure, e.g., a carbohydrate moiety-containing matrix. For example, the method can be used to prevent binding of a cell or protein to the carbohydrate-moiety displaying cell, tissue, or biological structure. For example, the antibody can be used to treat a leukocyte-migration disorder, e.g., an inflammatory disorder, or an endothelial cell-based disorder, e.g., a disorder associated with excessive angiogenesis, e.g., a cancer (e.g., a metastatic cancer), or a cardiovascular disorder, e.g., atherosclerosis. In one embodiment that relates to a cancerous disorder, the antibody binds to an epitope of a tumor (cancer) glycosidic antigens, e.g., an antigen present on a tumor cell in at least 2, 5, or 10 fold greater abundance than on a normal cell, an antigen the glycolipid class, including acidic glycolipid such as, for example, gangliosides GD2, GD3 and GM3 (melanoma) and neutral glycolipids such as, for example, the Lewis$^y$ (Le$^y$) (breast, prostate, ovary) and the Globo H (breast, prostate, ovary) antigens, and/or sialylated derivatives thereof; O-glycosyl peptides (or aminoacid) class such as, for example, the Tn antigen ($\alpha$GalNAc-Ser or $\alpha$Gal NAc-Thr), T* antigen ($\beta$Gal-(1-3)-$\alpha$-GalNac-Ser or $\beta$Gal(1-3) $\alpha$CalNAc-Thr)- (see, e.g., Springer G. F. *Science* 224, 1198-1206 (1984)) (ovary, breast, lung), or di-Tri ($\alpha$ GalNAc-Ser/Thr)$_2$, tri-Tn($\alpha$ GalNac-Ser/Thr)$_3$ or hexa-Tn($\alpha$GalNAc-Ser/Thr)$_6$. An antibody can be conjugated to a toxin, e.g., a cytotoxin or a radionucleoside, to kill, ablate, or otherwise inhibit a tumor cell. The antibody can be administered to a subject, e.g., a human subject, in need of such treatment, e.g., in amount effective and/or for a time effective to ameliorate such a disorder, e.g., to reduce tumor size and/or migration.

An antibody to a carbohydrate moiety that is presented by a bacterial cell can be used, e.g., to treat or prevent a disorder associated with a bacterial infection. For example, the epitope recognized by the antibody can be an epitope of a pathogenic bacteria, e.g., *Salmonella*. One *Salmonella* antigen is the serogroup B O-chain polysaccharide. Other exemplary epitopes include those on capsular bacterial polysaccharides selected from the group consisting of *Neisseria* meningitis, *Haemophilus influenza; Streptococcus pneumoniae* and other *Strepcoccus* species. Accordingly, the antibody can be used to treat infections or other disorders associated with a bacterial pathogen, e.g., a bacteria of such species.

Diagnostic Uses

Antibodies identified by the methods described herein (e.g., antibodies that bind to carbohydrates) can be used in a diagnostic method. For example, such an antibody can be used to detect a target molecule (e.g., a carbohydrate) in vitro (e.g., a biological sample, such as tissue, biopsy, e.g., a cancerous tissue) or in vivo (e.g., in vivo imaging in a subject). For example, it may be useful to locate regions within a subject where a particular carbohydrate or other moiety is present.

An exemplary method includes: (i) contacting a sample with the antibody; and (ii) detecting formation of a complex between the antibody and the sample. The method can also include contacting a reference sample (e.g., a control sample) with the antibody, and determining the extent of formation of the complex between the protein and the sample relative to the same for the reference sample. A change, e.g., a statistically significant change, in the formation of the complex in the sample or subject relative to the control sample or subject can be indicative of the presence of the target molecule in the sample.

Another method includes: (i) administering the antibody to a subject; and (iii) detecting the protein in the subject, for example using in vivo imaging or other monitoring. The detecting can include determining localization of the protein in the subject.

The antibody can be directly or indirectly labeled with a detectable substance to facilitate detection. Exemplary detectable substances include various enzymes, prosthetic groups, fluorescent materials, luminescent materials, MRI contrast agents (such as chelates that can attach paramagnetic substances), and radioactive materials.

The following examples, which should not be construed as further limiting, illustrate further embodiments. The contents of all references, pending patent applications and published patents, cited throughout this application are hereby expressly incorporated by reference.

EXAMPLES

Example 1

Library Construction

An antibody library that includes antibodies with properties biased for interaction with charged carbohydrates is constructed as follows. The library is constructed by modifying the antibody coding nucleic acids from a more general antibody library, the "FAB-310 library" (Hoet et al. 2005). The Fab-display cassette of FAB-310 is shown in FIG. 3. FIG. 3 illustrates a representative Fab with the useful restriction sites: ApaLI, AscI, SfiI, XbaI, BstEII, and NotI. The FAB-310 antibody library includes synthetic diversity at HC CDR1 and HC CDR2 in a VH3-23 framework (at HC positions 31, 33, 35, 56 and 58, any amino-acid type except cysteine was allowed; at HC positions 50 and 52, Y, R, W, G, V, and S were allowed; and at position HC 52a, P and S were allowed). It includes natural diversity at HC CDR3 and throughout the LC region (kappa and lambda light chains (LC) from 35 donors who had one or more autoimmune conditions were used). Antibody coding nucleic acids from the FAB-310 antibody library are modified by replacing the segment encoding HC FR3::CDR3 with synthetic oligonucleotides with the following design:

For the(R/K)-(G/S)-X-(R/K)-X-(K/R)-X (SEQ ID NO:10) motif the following codons were used:

ARG|RGT|NNK|ARG|NNK|ARG|NNK.    (SEQ ID NO: 4)

where K=T&G, N=A, G, C, T, and R=A&G.

The region in which the HC CDR3 resides is diagrammed as follows:

```
   Y   L   Q   M   N   S   L   R   A   E   D   T   A   V   Y   Y   C
  |tac|ttg|cag|atg|aac|agC|TTA|AGg|gct|gag|gac|aCT|GCA|Gtc|tac|tat|tgt|
  FR3-------------------------------------------------------------------

A  R/K G/S  X  R/K  X  R/K  X   W   G   Q   G   T   L   V   T   V   S
  |gct|aRg|Rgt|NNK|ARG|NNK|ARG|NNK|TGG|GGC|CAA|GGT|ACC|CTG|GTC|ACC|gtc|tct
  FR3---- <------CDR3------------>

S   (SEQ ID NO: 12)

Agt|  (SEQ ID NO: 11)
```

The following primers are used:
Primer 1 (to amplify the first PCR product, anneals in FR4 of HC)

5'AGC|ACA|ATA|GTA|GAC|TGC|AGT|GTC|   (SEQ ID NO: 18)

CTC|AGC|CCT|TAA|GCT|GTT|CAT|CTG|CAA|

GTA 3'

Primer 2 (anneals in FR4 of HC, brings the HC-CDR3 diversity)

5'ACT|AGA|GAC|GGT|GAC|CAG|GGT|ACC|   (SEQ ID NO: 19)

TTG|GCC|CCA|MNN|CYT|MNN|CYT|MNN|ACY|

CYT|AGC|ACA|ATA|GTA|GAC|TGC|AGT 3'

The library is assembled using two rounds of PCR. In the first reaction, a nucleic acid segment encoding synthetic CDR1-CDR2 is amplified from plasmid DNA using pUC reverse (5'-AGC GGA TAA CAA TTT CAC ACA GG-3' (SEQ ID NO:20), beyond BstEII in pMID21) and primer #1 for 15 cycles. In a second reaction, the products of the first reaction are amplified with a $C_{kappa}$ forward primer (5'-CCA TCT GAT GAG CAG TTG AAA TCT-3' (SEQ ID NO:21), shown in Table 50) and primer #2 for 15 cycles. The product of the second reaction is digested with restriction enzymes SfiI-BstEII and ligated into corresponding sites in the antibody coding library FAB-310 kappa and lambda plasmid DNA.

This result of these manipulations is a specialized FAB-310 library that differs in H-CDR3 sequence from the parental FAB-310 library (see FIG. 1).

Example 2

Library Construction

An antibody library that included antibodies with properties biased for interaction with carbohydrates was constructed. We modified antibody coding nucleic acids from a more general antibody library, the "FAB-310 library" described in Example 1. Antibody coding nucleic acids from the FAB-310 antibody library were modified by replacing the segment encoding HC CDR3 with synthetic oligonucleotides with the following design:
For the G X R X K/R X (SEQ ID NO:13) motif the following codons were used:

GGA|MNN|CGA|MNN|ARR|MNN.   (SEQ ID NO: 14)

where M=A&C, N=A,G,C,T, and R=A&G.
The region in which the HC CDR3 resides is diagrammed as follows:

```
   Y   L   Q   M   N   S   L   R   A   E   D   T   A   V   Y   Y   C
  |tac|ttg|cag|atg|aac|agC|TTA|AGg|gct|gag|gac|aCT|GCA|Gtc|tac|tat|tgc|

A   R   G   X   R   X  K/R  X   W   G   Q   G   T   L   V
  |gct|aga|GGA|MNN|CGA|MNN|ARR|MNN|TGG|GGC|CAA|GGT|ACC|CTG|GTC|
           <------CDR3------------>

T   V   S   S    (SEQ ID NO: 16)

ACC|gtc|tct|Agt|  (SEQ ID NO: 15)
```

The MNN codons allow the amino-acid types: L, P, Q, H, R, I, M, T, N, and S. The following primers were used:

Primer 1
5' TCCTCTAGCGCAATAGTAGACTGCAGTGTCCTC (SEQ ID NO: 22)
AGCCCTTAAGCTGTTCATCTGCAAGTA 3'

Primer 2
5' ACTAGAGACGGTGACCAGGGTACCTTGGCCCCA (SEQ ID NO: 23)
NNKYYTNNKTCGNNKTCCTCTAGCGCAAT
AGTAGAC 3'

Figure 2:
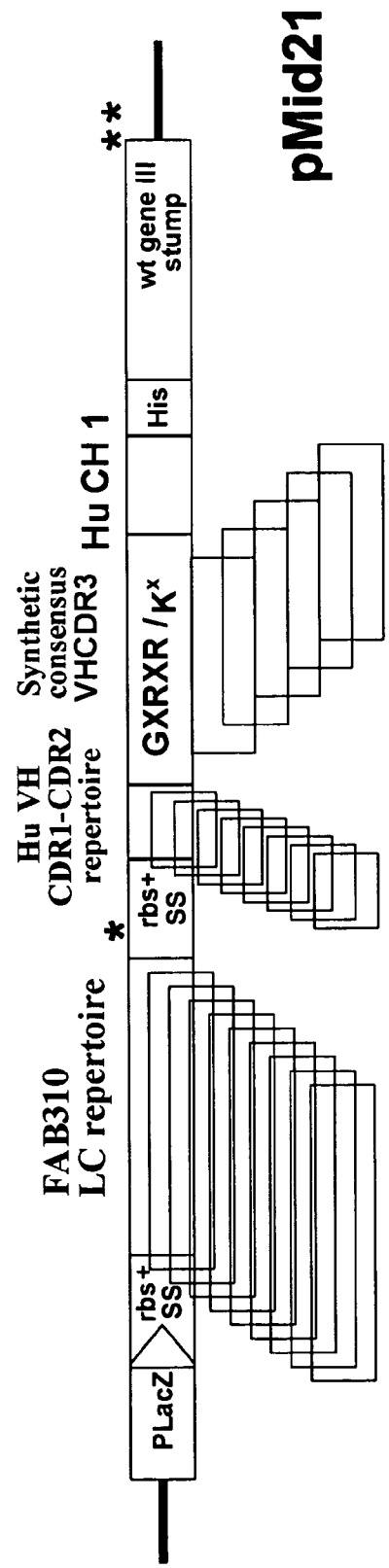
FIG. 2 is a schematic of the Library of Example 2. The Fab display cassette having captured kappa and lambda LC and synthetic diversity in HC CDR1 and CDR2 is as described in Hoet et al. (Nature Biotechnology, 2005, 23(3):344-8. HC CDR3 is as described in Example 2.
Figure 4A:
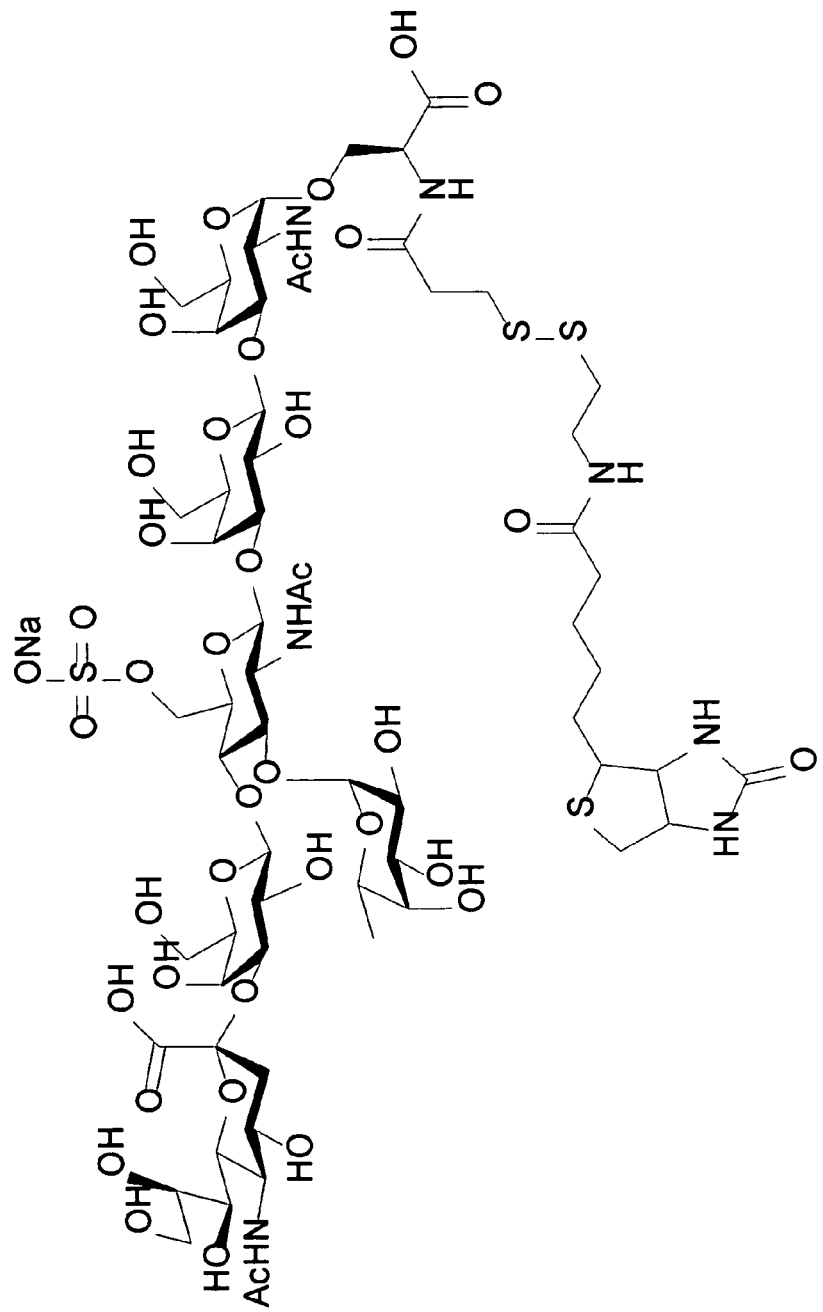
FIGS. 4A, 4B, 4C and 4D are the structures of the sulfocore 1 and sulfocore 6 carbohydrate moieties and their non-sulfated counterparts core 1 and core 6. Their respective molecular weights are mentioned below the carbohydrate structure.
Figure 4B:
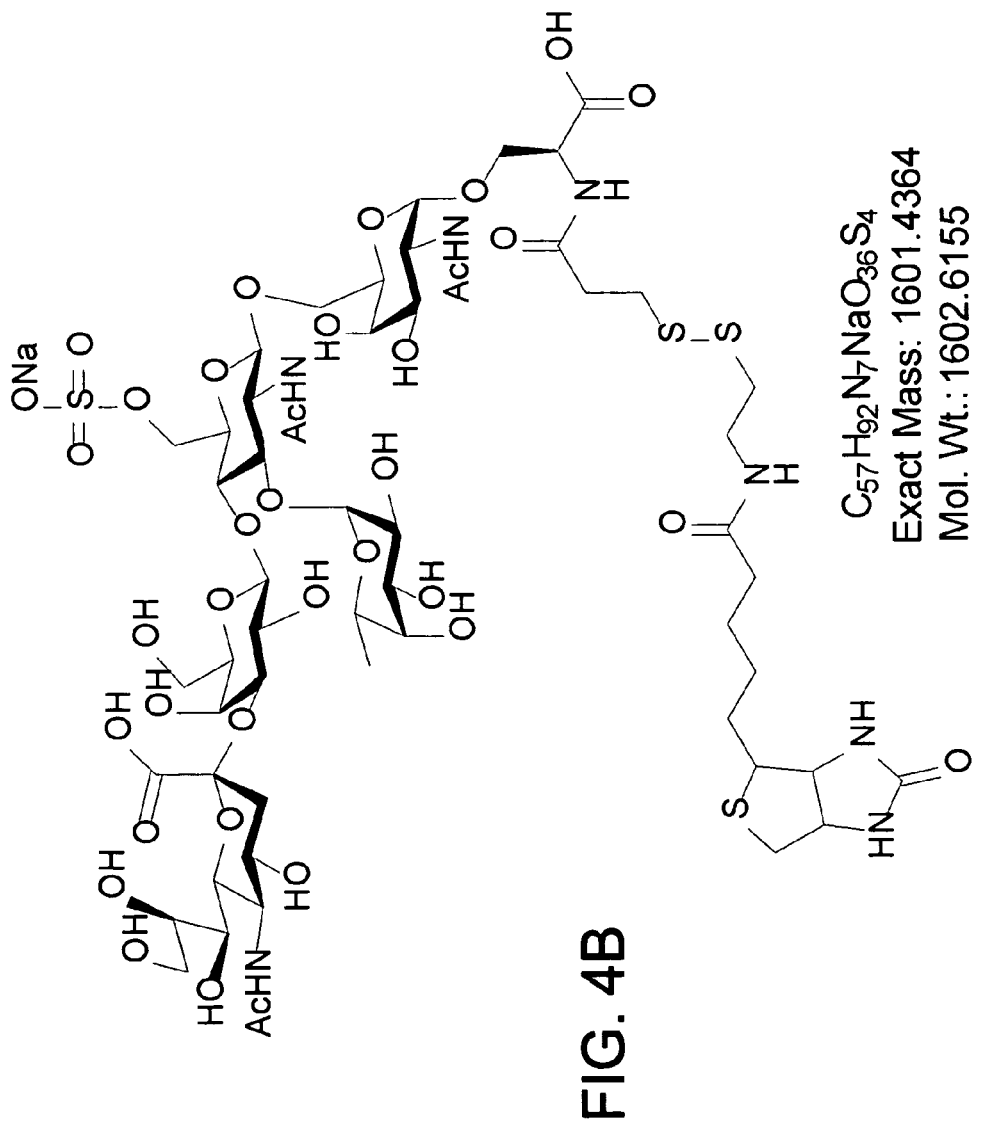
Figure 4C:
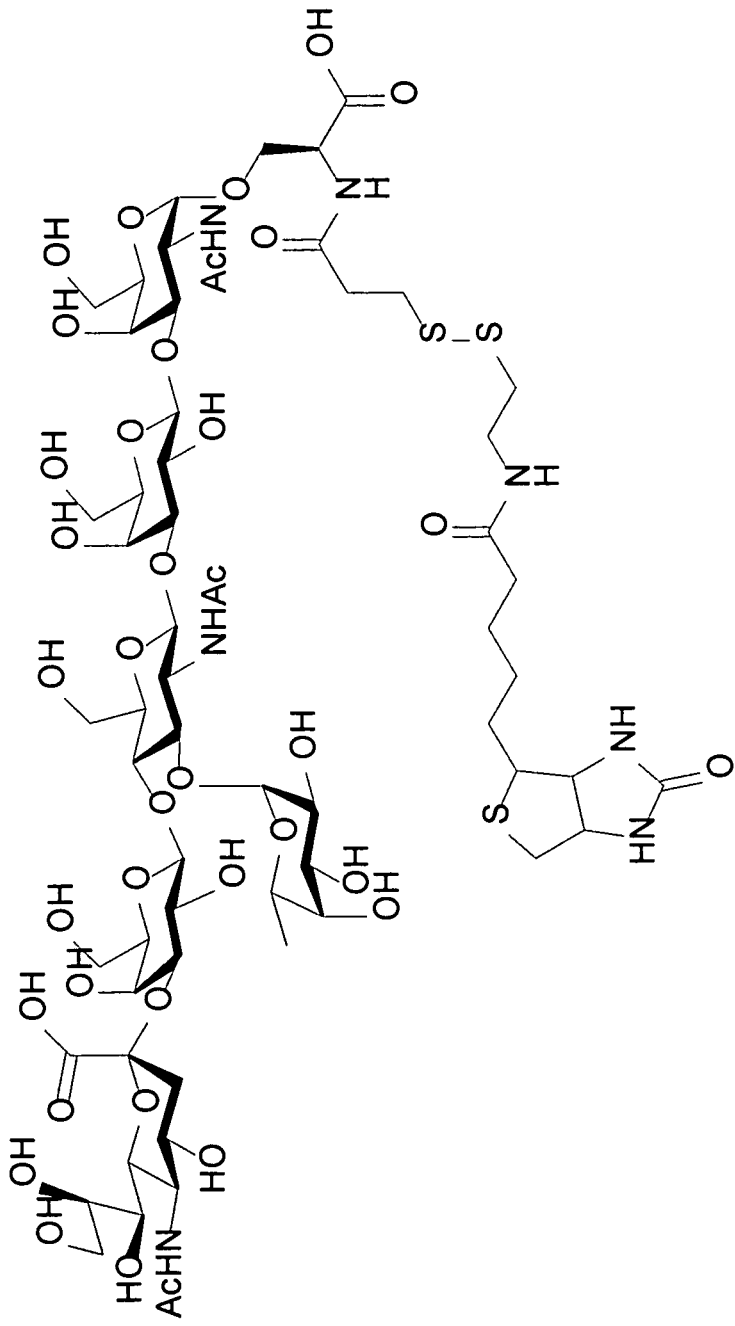
Figure 4D:
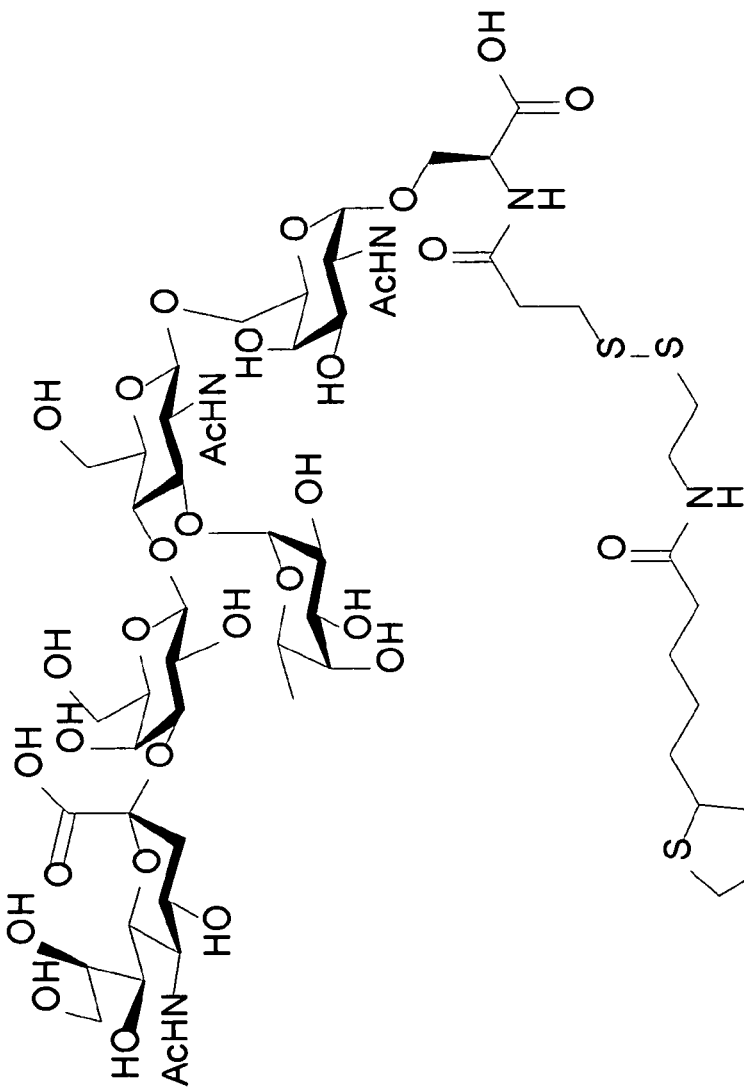

The library, as shown in FIG. 2, was assembled using two rounds of PCR. In the first reaction, a nucleic acid segment encoding synthetic CDR1-CDR2 was amplified from plasmid DNA using pUC reverse and primer #1 for 15 cycles. In a second reaction, the products of the first reaction were amplified with a $C_{kappa}$ forward primer and primer #2 for 15 cycles. The product of the second reaction was digested with restriction enzymes SfiI-BstEII and ligated into corresponding sites in the antibody coding library FAB-310 kappa and lambda plasmid DNA.

This result of these manipulations was a specialized FAB-310 library that differs only in H-CDR3 sequence from the parental FAB-310 library. The number of transform ants obtained for the antibody coding library was about $2 \times 10^9$.

Example 3

Selection of Antibodies from a Designed Antibody Library

The library can be used to select antibodies that bind to various carbohydrate moieties (especially negatively charged carbohydrates), phosphopeptides, or any target.

The library can be selected using, for example, 1, 2, or 3 rounds of selection in which the target is a compound that includes a negatively charged carbohydrate moiety. Three rounds of selection can be performed using 100-fold more phage than the number of library transformants.

The targets can be immobilized on beads prior to incubation with the phages. At least two selection strategies can be employed. For one exemplary selection, the target is directly coated to immunotubes in $(NH_4)_2 SO_4$ 90% saturated at pH5.5. For the other selection, the target is spotted on a nitrocellulose membrane which is blocked with BSA or other suitable blocker and selection is performed on this nitrocellulose membrane.

Nonspecific binders can sometimes be found. These bind many antigens and are found because phage sometimes bind to the target membrane or well independent of the target material. However, inclusion of a step to deplete library members on streptavidin and high throughput screening could be used to aid finding specific antibodies.

We conclude that antibodies that bind to negatively charged carbohydrate can successfully be isolated from an antibody library that includes CDR3 sequences with properties favourable for carbohydrate binding. We identified antibodies that specifically bind to certain target compound and that do not detectably interact a non-target compound or control antigen. When using heparan sulfate, the enrichment factors were 1600-fold when the heparan sulfate compound is immobilized using immunotubes.

Example 4

Library Construction

An antibody library that included antibodies with properties biased for interaction with carbohydrates was constructed, using the human semisynthetic antibody phage display library FAB-310 (Hoet et al., 2005). The FAB-310 library uses V-gene (V3-23) as scaffold protein with natural HC-CDR3 diversity and synthetic HC-CDR1-CDR2 diversity, which are respectively 5 and 15 amino-acid residues in length. The heavy chains are combined with a natural repertoire of kappa and lambda human light chains. The library has a size of $3.5 \times 10^{10}$.

The carbohydrate-biased library was constructed to incorporate the sequence R/K-G/S-X-R/K-X-R/K-X (SEQ ID NO:17) into HC-CDR3. 10 ng of FAB-310 Kappa-HC library was used as a template for a PCR reaction using a Kappa constant forward primer.

The HC-CDR3 was designed with the following amino-acid sequence G/S X R/K X R/K X (SEQ ID NO:9). The oligonucleotide (HC-CDR3 primer) supporting this sequence carry the following nucleotide sequence 10 ng DNA of the FAB 310 Kappa-HC repertoire were used as template of a PCR reaction using a Kappa constant forward primer (5'-CCATCTGATGAGCAGTTGAAATCT-3' (SEQ ID NO:21)) as 5' end primer and the HC-CDR3 primer (5'-ACTA-GAGACGGTGACCAGGGTACCTTGGC-CCCAMNNCYTMNNCYTMNNACYCYTAG-CACAATAGTAGACTGCAGT-3' (SEQ ID NO:19)) as 3' end primer in order to amplify the full HC repertoire. PCR was performed for 35 cycles in a 25 μl format using Advantage 2 DNA polymerase (Clontech) (1 min at 95° C., 1 min at 50° C. and 2 min at 68° C.). 10 μg of the 650 bp generated fragment were digested with 4 U/μg of BstEII restriction endonuclease (NEB) followed by a cleavage with 10 U/μg XbaI. A 140 bp fragment containing the HC-CDR3 repertoire was gel purified. One and a half micrograms of the resulting DNA fragment was ligated into 6 μg of similarly cut phagemid vector pMID21 (containing both the kappa ad lambda light chain repertoires) using $T_4$ DNA ligase (NEB) at a 1:4 vector:insert ratio. 2.5 μg of desalted λHC-ligation mixture and 2.5 μg of the κHC mixture were separately electroporated into the *E. coli* strain TG1 using 100 ng of ligation mixture per electroporation event. The Fab library has a size of $2 \times 10^9$ representants.

The library was checked for quality by PCR amplifying the Fab antibody cassette as described in Shoonbroodt et al. (2005, *Nucl. Acids Res.* 33(9):e81), and sequencing the amplified products.

Example 5

Selection, Screening, and Sequencing of Antibodies Specific for Carbohydrate Antigens Antibodies specific to carbohydrate antigens were selected from the library described in Example 2. Although this library has reduced diversity as compared to the libraries described in Examples 1 and 3, the library is nonetheless biased for interaction with carbohydrates.

Selection

Phagemid particles were rescued with with helper phage M13-KO7 according to Marks et al. (1991 *J. Mol. Biol.* 222 (3):581-97) on a 3-liter scale. Three library selections were performed (1) sulfocore 6 (SC6), (2) sulfocore 1 (SC 1), and (3) a combination of heparan sulfate (HS) and chemically desulfated N-sulfated heparin (CDSNS). The chemical structure of SC1 and SC6 and their non-sulfated counterparts are shown in FIG. 4.

The 6-sulfo sialyl Lewis X glycans correspond to the L-selectin ligand "sulfoadhesin." SC6 selection was performed using $10^{13}$ phages which had been pre-incubated for 1 hour in 2% Marvel PBS at room temperature (RT). 500 nM SC6 antigen, which had been modified by addition of a serine residue to $carbon_6$ and coupling to a biotin molecule, was captured on magnetic streptavidin Dynabeads (Dynal), blocked with 2% Marvel PBS, then added to the blocked phages. After several washing steps, phages were eluted with 100 mM TEA and neutralized in 1 M Tris-HCl (pH7.4). Eluted phages were used to infect *E. coli* TG1 cells. Two additional rounds of selection were performed, for a total of three rounds, under the same conditions.

SC1 selection was carried out essentially the same as the selection for SC6.

HS and CDSNS were immobilized on immunotubes (MAXISORP™, Nunc) by incubation with a 100 μg/mL mixture of HS and CDSNS in 90% saturated $(NH_4)_2SO_4$ buffer. Immunotubes and $10^{13}$ phage were blocked separately for 30 minutes with 1% BSA, 0.05% Tween-20 in PBS. The blocked phage preparation was then incubated with the target in the tubes for 30 minutes on a rotator followed by 90 minute incubation standing at RT. Tubes were washed 10 times with 0.05% TWEEN® 20 in PBS, followed by 10 times with PBS. Phage were eluted in 100 mM TEA, then immediately neutralized with 1M Tris, pH7.4. Eluted phages were used to infect *E. coli* TG1 cells. The selection was repeated an additional two rounds (for a total of three) under the same conditions except that wash steps were performed 20 times.

Screening

Phage-displaying Fab eluted from the third round of selection were recovered, propagated, and isolated as individual clones. Culture supernatants containing phage-displaying Fab were tested by ELISA. Fab from the SC6 selection were assayed against biotinylated SC6 indirectly captured via immobilized BSA-streptavidin (MAXISORP, Nunc). Plates were coated with 50 ng SC6 per well (biotinylated) in PBS. 50 ng C6 (non-sulfated core 6) or 500 ng streptavidin per well were used as negative controls. Fab from the SC1 selection were screened essentially as for SC6, but using SC1 as the antigen. HS-binding Fab were assayed using plates was coated with 500 ng per well of a mix of HS/CDSNS (in 90% $(NH_4)_2SO_4$) or 100 ng BSA (as negative control). Plates were coated overnight at 4° C. Plates were washed three times with PBS-TWEEN®20 0.05% (PBST), blocked with 2% Marvel in PBS (MPBS), then washed three times with PBST before use. Phages were incubated with the antigen for one hour at RT, then removed and the plates were washed six times with PBST. Anti-M13 HRP antibody (APB) diluted 5000× in PBS was added for one hour, followed by six washes with PBST. Optical density at 450 nm ($OD_{450}$) was measured after development with TMB substrate. A number of clones which bound to to SC6 or HS were identified in the screening, but no Fabs binding SC1 were identified. It is expected that selection of the libraries described in Examples 1 and 4 would identify SC1-specific Fabs, in view of the increased diversity fo these libraries in comparison with the library described in Example 2.

Sequencing

Fab from clones giving a positive signal in ELISA (more than 2 times>background) were amplified using 5' and 3' backbone primers and the PCR products were sequenced for both light and heavy chains. Antibodies to SC6 did not react in ELISA with C6, SC1 and C1 (related structures), clearly showing the specificity of these antibodies to SC6.

We identified antibodies that specifically bind to heparan sulfate and that do not detectably interact with another sulfated carbohydrate or control antigen. Three distinct antibodies were identified, designated 1HS, 2HS, and 3HS. The heavy chain (HC) and light chain (LC) variable region amino acid sequences are shown in Table 1, and the CDR amino acid sequences are shown in Table 2.

TABLE 1

| Fab | Heavy Chain (HC) | Light Chain (LC) |
|---|---|---|
| 1HS | EVQLLESGGGLVQPGGSLRLSCAASGFTF SNYTMAWVRQAPGKGLEWVSSISSSGGHT PYADSVKGRFTISRDNSKNTLYLQMNSLR AEDTAVYYCARGKRNRN (SEQ ID NO: 33) | QDIQMTQSPDSLAVSLGERATINCKSSQSVLYS SNNKNYLAWYQQKPGQPPKLLIYWASTRESGVP DRFSGSGSGTDFTLTISSLQAEDVAVYYCQQYY STPPT (SEQ ID NO: 34) |
| 2HS | EVQLLESGGGLVQPGGSLRLSCAASGFTF SGYRMNWVRQAPGKGLEWVSSIGSSGGHT SYADSVKGRFTISRDNSKNTLYLQMNSLR AEDTAVYYCARGKRNRT (SEQ ID NO: 35) | QDIQMTQSPGTLSLSPGERATLSCRASQSVSSS YLAWYQQKPQAPRLLIYGASSRATGIPDRFSG SGSGTDFTLTISRLEPEDFAVYYCQQYGSSPRT (SEQ ID NO: 36) |
| 3HS | EVQLLESGGGLVQPGGSLRLSCAASGFTF SEYIMSWVRQAPGKGLEWVSYISPSGGTT KYADSVKGRFTISRDNSKNTLYLQMNSLR AEDTAVYYCARGRRTKH (SEQ ID NO: 37) | QDIQMTQSPLSSLPVTLGQSASISCRSSQSLVHS DGNTYLNWFQQRPGQSPRRLIYKVSNRDSGVPD RFSGSGSGTDFTLKISRVEAEDVGVYYCMQGTH WPYT (SEQ ID NO: 38) |

TABLE 2

| | | CDR1 | CDR2 | CDR3 |
|---|---|---|---|---|
| 1HS | HC | NYTMA (SEQ ID NO: 39) | SISSSGGHTPYADSVKG (SEQ ID NO: 40) | GKRNRN (SEQ ID NO: 41) |
| 2 | HC | GYRMN (SEQ ID NO: 42) | SIGSSGGHTSYADSVGK (SEQ ID NO: 43) | GKRNRT (SEQ ID NO: 44) |
| 3HS | HC | EYIMS (SEQ ID NO: 45) | YISPSGGTTKYADSVKG (SEQ ID NO: 46) | GRRTKH (SEQ ID NO: 47) |
| 1HS | LC | KSSQSVLYSSNNKNYLA (SEQ ID NO: 48) | WASTRES (SEQ ID NO: 49) | QQYYSTPPT (SEQ ID NO: 50) |
| 2 HS | LC | RASQSVSSSYLA (SEQ ID NO: 51) | GASSRAT (SEQ ID NO: 52) | QQYGSSPRT (SEQ ID NO: 53) |
| 3 HS | LC | RSSQSLVHSDGNTYLN (SEQ ID NO: 54) | KVSNRDS (SEQ ID NO: 55) | MQGTHWPY (SEQ ID NO: 24) |

At least sixteen clones showed specific binding to SC6 (as compared to binding to BSA, streptavidin, and unrelated sulfated carbohydrates). After sequencing, four distinct antibodies were identified, designated 1SC6, 2SC6, 3SC6, and 4SC6. Sequences of the HC and LC variable regions (both nucleotide and amino acid) are shown in Table 3, and CDR amino acid sequences are shown in Table 4.

TABLE 3

| Antibody | Nucleotide Sequence | Amino Acid Sequence |
|---|---|---|
| 1SC6 LC | CAGAGCGTCTTGACTCAGCCACCCTCAGTGTC<br>AGTGGCCCCAGGAAGGACGGCCACCATTACCT<br>GTGGGGGAAAAAACATTGGAGCTAAAAGTGTC<br>AACTGGTACCAACAGAGGCCAGGCCAGGCCCC<br>TGTCCTGGTCATCTTCTATGATACCGACCGGC<br>CCGCAGGAATAACTGGGCGATTGTCTGGCTCC<br>AATTCTGGGAACTCGGCCACCCTGACCATCAG<br>CAGGGTCGAGGCCGGGGACGAGGCCGATTATT<br>ACTGTCAGGTGTGGGGTGTCAGTGGTGATCAT<br>CCGGTTTTCGGCGGAGGGACTAGGCTGACCGT<br>CCTGGGTCAGCCC<br>(SEQ ID NO: 56) | QSVLTQPPSVSVAPGRTATITCGGKNI<br>GAKSVNWYQQRPGQAPVLVIFYDTDRP<br>AGITGRLSGSNSGNSATLTISRVEAGD<br>EADYYCQVWGVSGDHPVFGGGTRLTVL<br>GQP<br>(SEQ ID NO: 57) |
| 1SC6 HC | GAAGTTCAATTGTTAGAGTCTGGTGGCGGTCT<br>TGTTCAGCCTGGTGGTTCTTTACGTCTTTCTT<br>GCGCTGCTTCCGGATTCACTTTCTCTGGTTAC<br>ATGATGGCTTGGGTTCGCCAAGCTCCTGGTAA<br>AGGTTTGGAGTGGGTTTCTTGGATCTCTCCTT<br>CTGGTGGCTTTACTAAGTATGCTGACTCCGTT<br>AAAGGTCGCTTCACTATCTCTAGAGACAACTC<br>TAAGAATACTCTCTACTTGCAGATGAACAGCT<br>TAAGGGCTGAGGACACTGCAGTCTACTATTGC<br>GCTAGAGGAAGCCGACTCAGGCAT<br>(SEQ ID NO: 58) | EVQLLESGGGLVQPGGSLRLSCAASGF<br>TFSGYMMAWVRQAPGKGLEWVSWISPS<br>GGFTKYADSVKGRFTISRDNSKNTLYL<br>QMNSLRAEDTAVYYCARGSRLRH<br>(SEQ ID NO: 59) |
| 2SC6 LC | CAAGACATCCAGATGACCCAGTCTCCATCCTC<br>CCTGTCTGCATCTGTAGGAGACAGAGTCACCA<br>TCACTTGCCGGGCAAGTCAGGGCATTAGAAAT<br>GATTTAGGCTGGTATCAGCAGAAACCAGGGAA<br>AGCCCCTAAGCGCCTGATCTATGCTGCATCCA<br>GTTTGCAAAGTGGGGTCCCATCAAGGTTCAGC<br>GGCAGTGGATCTGGGACAGAATTCACTCTCAC<br>AATCAGCAGCCTGCAGCCTGAAGATTTTGCAA<br>CTTATTACTGTCTACAGCATAATAGTTACCCG<br>TACACTTTTGGCCAGGGGACCAAGCTGGAGAT<br>CAAACG<br>(SEQ ID NO: 60) | QDIQMTQSPSSLSASVGDRVTITCRAS<br>QGIRNDLGWYQQKPGKAPKRLIYAASS<br>LQSGVPSRFSGSGSGTEFTLTISSLQP<br>EDFATYYCLQHNSYPYTFGQGTKLEIK<br>(SEQ ID NO: 61) |
| 2SC6 HC | GAAGTTCAATTGTTAGAGTCTGGTGGCGGTCT<br>TGTTCAGCCTGGTGGTTCTTTACGTCTTTCTT<br>GCGCTGCTTCCGGATTCACTTTCTCTGGTTAC<br>ATGATGCAGTGGGTTCGCCAAGCTCCTGGTAA<br>AGGTTTGGAGTGGGTTTCTTCTATCTCTCCTT<br>CTGGTGGCTTTACTGAGTATGCTGACTCCGTT<br>AAAGGTCGCTTCACTATCTCTAGAGACAACTC<br>TAAGAATACTCTCTACTTGCAGATGAACAGCT<br>TAAGGGCTGAGGACACTGCAGTCTACTATTGC<br>GCTAGAGGACGGCGACACAGGAAT<br>(SEQ ID NO: 62) | EVQLLESGGGLVQPGGSLRLSCAASGF<br>TFSGYMMQWVRQAPGKGLEWVSSISPS<br>GGFTEYADSVKGRFTISRDNSKNTLYL<br>QMNSLRAEDTAVYYCARGRRHRN<br>(SEQ ID NO: 63) |
| 3SC6 LC | CAAGACATCCATATGACCCAGTCTCCAGGCAC<br>CCTGTCTTTGTCTCCAGGGGAAAGAGCCACCC<br>TCTCCTGCAGGGCCAGTCAGAGTATTAGCAAC<br>ACCTACTTAGCCTGGTACCAGCAGAAACCTGG<br>CCAGGCTCCCAGGCTCCTCATCTATGGTGCAT<br>CCAGCAGGGCCACTGGCATCCCAGACAGGTTC<br>AGTGGCAGTGGGTCTGGGACAGACTTCACTCT<br>CACCATCAGCAGGCTGGAGCCTGAAGATTTTG<br>CAGTGTATTACTGTCAGCAGTATGGTAGCTCA<br>CCCCTGTACACTTTTGGCCAGGGGACCAAGTT<br>GGAGATCAAA<br>(SEQ ID NO: 64) | QDIHMTQSPGTLSLSPGERATLSCRAS<br>QSISNTYLAWYQQKPGQAPRLLIYGAS<br>SRATGIPDRFSGSGSGTDFTLTISRLE<br>PEDFAVYYCQQYGSSPLYTFGQGTKLE<br>IK<br>(SEQ ID NO: 65) |
| 3SC6 HC | GAAGTTCAATTGTTAGAGTCTGGTGGCGGTCT<br>TGTTCAGCCTGGTGGTTCTTTACGTCTTTCTT<br>GCGCTGCTTCCGGATTCACTTTCTCTGGTTAC<br>ATGATGAATTGGGTTCGCCAAGCTCCTGGTAA<br>AGGTTTGGAGTGGGTTTCTTCTATCGGTCCTT<br>CTGGTGGCTATACTACTTATGCTGACTCCGTT | EVQLLESGGGLVQPGGSLRLSCAASGF<br>TFSGYMMNWVRQAPGKGLEWVSSIGPS<br>GGYTTYADSVKGHFTISRDNSKNTLYL<br>QMNSLRAEDTAVYYCARGLRMNK<br>(SEQ ID NO: 67) |

TABLE 3-continued

| Antibody | Nucleotide Sequence | Amino Acid Sequence |
|---|---|---|
| | AAAGGTCACTTCACTATCTCTAGAGACAACTC TAAGAACACTCTCTACTTGCAGATGAACAGCT TAAGGGCTGAGGACACTGCAGTCTACTATTGC GCTAGAGGACTGCGAATGAAAAAG (SEQ ID NO: 66) | |
| 4SC6 LC | CAGAGCGTCTTGACTCAGGACCCTGCTGTGTC TGTGGCCTTGGGACAGACAGTCAGGATCACAT GCCAAGGAGACAGCCTCAGAAGCTATTATGCA AGCTGGTACCAGCAGAAGCCAGGACAGGCCCC TGTACTTGTCATCTATGGTAAAAACAACGGC CCTCAGGGATCCCAGACCGATTCTCTGGCTCC AGCTCAGGAAACACAGCTTCCTTGACCATCAC TGGGGCTCAGGCGGAAGATGAGGCTGACTATT ACTGTAACTCCCGGGACAGCAGTGGTAACATC TGGAAGGTATTCGGCGGAGGGACCAAGCTGAC CGTCCTAGGTCAGCCC (SEQ ID NO: 68) | QSVLTQDPAVSVALGQTVRITCQGDSL RSYYASWYQQKPGQAPVLVIYGKNNRP SGIPDRFSGSSSGNTASLTITGAQAED EADYYCNSRDSSGNIWKVFGGGTKLTV LGQP (SEQ ID NO: 69) |
| 4SC6 HC | GAAGTTCAATTGTTAGAGTCTGGTGGCGGTCT TGTTCAGCCTGGTGGTTCTTTACGTCTTTCTT GCGCTGCTTCCGGATTCACTTTCTCTGTTTAC CCTATGCATTGGGTTCGCCAAGCTCCTGGTAA AGGTTTGGAGTGGGTTTCTTATATCGGTTCTT CTGGTGGCGAGACTATGTATGCTGACTCCGTT AAAGGTCGCTTCACTATCTCTAGAGACAACTC TAAGAATACTCTCTACTTGCAGATGAACAGCT TAAGGGCTGAGGACACTGCAGTCTACTATTGC GCTAGAGGAAAACGAAACAAAGA (SEQ ID NO: 70) | EVQLLESGGGLVQPGGSLRLSCAASGF TFSVYPMHWVRQAPGKGLEWVSYIGSS GGETMYADSVKGRFTISRDNSKNTLYL QMNSLRAEDTAVYYCARGKRNKR (SEQ ID NO: 71) |

TABLE 4

| | LC - CDR1 | LC - CDR2 | LC - CDR3 | Family | HC-CDR1 | HC-CDR2 | HC-CDR3 |
|---|---|---|---|---|---|---|---|
| 1SC6 | GGKNIGAKSVN (SEQ ID NO: 72) | YDTDRPA (SEQ ID NO: 76) | QVWGVSGDHPV (SEQ ID NO: 80) | VL3 | GYMMA (SEQ ID NO: 84) | WISPSGGFTKYADSVKG (SEQ ID NO: 88) | GSRLRH (SEQ ID NO: 92) |
| 2SC6 | RASQGIRNDLG (SEQ ID NO: 73) | AASSLQS (SEQ ID NO: 77) | LQHNSYPYT (SEQ ID NO: 81) | VK1 | GYMMQ (SEQ ID NO: 85) | SISPSGGFTEYADSVKG (SEQ ID NO: 89) | GRRHRN (SEQ ID NO: 93) |
| 3SC6 | RASQSISNTYLA (SEQ ID NO: 74) | GASSRAT (SEQ ID NO: 78) | QQYGSSPLYT (SEQ ID NO: 82) | VK3 | GYMMN (SEQ ID NO: 86) | SIGPSGGYTTYADSVKG (SEQ ID NO: 90) | GLRMKK (SEQ ID NO: 94) |
| 4SC6 | QGDSLRSYYAS (SEQ ID NO: 75) | GKNNRPS (SEQ ID NO: 79) | NSRDSSGNIWKV (SEQ ID NO: 83) | VL3 | VYPMH (SEQ ID NO: 87) | YIGSSGGETMYADSVKG (SEQ ID NO: 91) | GKRNKR (SEQ ID NO: 95) |

Other embodiments are within the following claims.

What is claimed is:

1. A method for identifying an antibody or fragment thereof that binds to a carbohydrate comprising:

a) providing a protein library comprising a plurality of diverse antibodies or fragments thereof, wherein said antibodies or fragments thereof comprise a heavy chain variable domain sequence and a light chain variable domain sequence, wherein said heavy chain variable domain sequence comprises diversity in HC CDR3, and wherein each antibody or fragment thereof comprises an HC CDR3 comprising (G/S)-X-(K/R)-X-(K/R)-X (SEQ ID NO:3), wherein X is varied among a set of amino acids that exclude basic amino acids;

b) contacting said protein library to a carbohydrate; and c) identifying one or more antibodies or fragments thereof that binds to said carbohydrate, wherein the protein library comprises at least $10^5$ antibodies or fragments thereof.

2. The method of claim 1, wherein X is selected from at least ten different amino acids.

3. The method of claim 1, wherein X is selected from at least four different amino acids.

4. The method of claim 1, wherein X represents a non-cysteine amino acid.

5. The method of claim 1, wherein said HC CDR3 region comprises less than 10 amino acids in length.

6. The method of claim 1, wherein said HC CDR3 comprises less than 8 amino acids in length.

7. The method of claim 1, wherein said heavy chain variable domain sequences of said antibodies comprise the same canonical structure.

8. The method of claim 7, wherein said canonical structure comprises that of the 3-23 heavy chain VH segment.

9. The method of claim 1, wherein the step of providing a protein library comprises constructing HC CDR3 using trinucleotide addition technology.

10. The method of claim 1, wherein said protein library comprises a phage display library, and the step of identifying one or more antibodies that interact with said carbohydrate comprises recovering one or more phage that encode an antibody that binds to the carbohydrate.

11. The method of claim 1, wherein the carbohydrate comprises a glycosaminoglycan.

12. A method for providing an antibody coding library biased for carbohydrate binding, comprising:
 a) providing an antibody coding library that includes a plurality of members, wherein each member comprises a sequence encoding a heavy chain variable domain sequence, wherein the HC variable domain coding sequences are diverse among members of the plurality;
 b) providing nucleic acids that encode a diverse population of HC CDR3s, wherein said HC CDR3 coding sequences encode HC CDR3s comprising (G/S)-X-(K/R)-X-(K/R)-X (SEQ ID NO:3), wherein X is varied among a set of amino acids that exclude basic amino acids; and
 c) modifying the HC variable domain coding sequences of said antibody coding library to include the HC CDR3 coding sequences; and
 d) obtaining an antibody coding library biased for carbohydrate binding, wherein the antibody coding library comprises at least $10^5$ nucleic acids.

13. The method of claim 12, wherein the step of providing nucleic acids that encode a diverse population of HC CDR3 sequences comprises constructing said nucleic acids using trinucleotide addition technology.

14. The method of claim 12, further comprising:
 e) expressing the members of the antibody coding library to obtain a library of proteins.

* * * * *